(12) United States Patent
Konduri et al.

(10) Patent No.: US 8,466,190 B2
(45) Date of Patent: Jun. 18, 2013

(54) POLYMORPHIC FORMS OF SUNITINIB BASE

(75) Inventors: Srinivasa Krishna Murthy Konduri, Hyderabad (IN); Bhujanga Rao Adibhatla Kali Satya, Hyderabad (IN); Nannapaneni Venkaiah Chowdary, Hyderabad (IN)

(73) Assignee: Natco Pharma Limited, Andhra Pradesh (IN)

( * ) Notice: Subject to any disclaimer, the term of this patent is extended or adjusted under 35 U.S.C. 154(b) by 37 days.

(21) Appl. No.: 12/988,173

(22) PCT Filed: Apr. 16, 2008

(86) PCT No.: PCT/IN2008/000248
§ 371 (c)(1),
(2), (4) Date: Dec. 9, 2010

(87) PCT Pub. No.: WO2009/128083
PCT Pub. Date: Oct. 22, 2009

(65) Prior Publication Data
US 2011/0105580 A1    May 5, 2011

(51) Int. Cl.
*A61K 31/4015* (2006.01)
*C07D 209/34* (2006.01)

(52) U.S. Cl.
USPC .......................... 514/414; 548/468

(58) Field of Classification Search
USPC .......................... 514/414; 548/468
See application file for complete search history.

(56) References Cited

FOREIGN PATENT DOCUMENTS

| WO | WO 01/60814 A2 | 8/2001 |
|---|---|---|
| WO | WO 03/016305 A1 | 2/2003 |
| WO | WO 03/070725 A2 | 8/2003 |
| WO | WO 2009/067674 A2 | 5/2009 |
| WO | WO 2009/074862 A1 | 6/2009 |
| WO | WO 2009/109388 A1 | 9/2009 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*
U.S. Appl. No. 60/989,560, filed Nov. 21, 2007.
U.S. Appl. No. 61/013,117, filed Dec. 12, 2007.
U.S. Appl. No. 61/030,167, filed Feb. 20, 2008.
U.S. Appl. No. 61/031,773, filed Feb. 27, 2008.
U.S. Appl. No. 61/041,439, filed Apr. 1, 2008.
U.S. Appl. No. 61/042,138, filed Apr. 3, 2008.
U.S. Appl. No. 61/045,196, filed Apr. 15, 2008.
U.S. Appl. No. 61/048,467, filed Apr. 28, 2008.
U.S. Appl. No. 61/048,460, filed Apr. 28, 2008.
U.S. Appl. No. 61/058,053, filed Jun. 2, 2008.
U.S. Appl. No. 61/058,417, filed Jun. 3, 2008.
U.S. Appl. No. 61/059,088, filed Jun. 5, 2008.
U.S. Appl. No. 61/059,222, filed Jun. 5, 2008.
U.S. Appl. No. 61/061,069, filed Jun. 12, 2008.
U.S. Appl. No. 61/061,920, filed Jun. 16, 2008.
U.S. Appl. No. 61/078,650, filed Jul. 7, 2008.
U.S. Appl. No. 61/082,405, filed Jul. 21, 2008.
U.S. Appl. No. 61/084,156, filed Jul. 28, 2008.
U.S. Appl. No. 61/085,991, filed Aug. 4, 2008.
U.S. Appl. No. 61/087,859, filed Aug. 11, 2008.
U.S. Appl. No. 61/088,554, filed Aug. 13, 2008.
U.S. Appl. No. 61/101,527, filed Sep. 30, 2008.
U.S. Appl. No. 61/108,078, filed Oct. 24, 2008.
U.S. Appl. No. 12/415,352, filed Mar. 31, 2009.
U.S. Appl. No. 12/717,481, filed Mar. 4, 2010.
U.S. Appl. No. 12/743,568, filed Nov. 21, 2008.
U.S. Appl. No. 12/747,762, filed Dec. 12, 2008.
U.S. Appl. No. 12/918,612, filed Mar, 4, 2009.
U.S. Appl. No. 13/055,609, filed Jul. 23, 2009.
Third-Party Observations Pursuant to Article 115 EPC, Nov. 22, 2012.

* cited by examiner

*Primary Examiner* — Shawquia Young
(74) *Attorney, Agent, or Firm* — Kilpatrick Townsend & Stockton LLP

(57) ABSTRACT

The present invention relates to novel polymorphic forms of N-[2-(diethylamino)ethyl]-5-[(5-fluoro-1,2-dihydro-2-oxo-3H-indol-3-ylidene)methyl-2,4-dimethyl-1H-pyrrole-3-carboxamide-Sunitinib base (I). The present invention also relates to methods of preparing such polymorphic crystals.

6 Claims, 21 Drawing Sheets

(I)

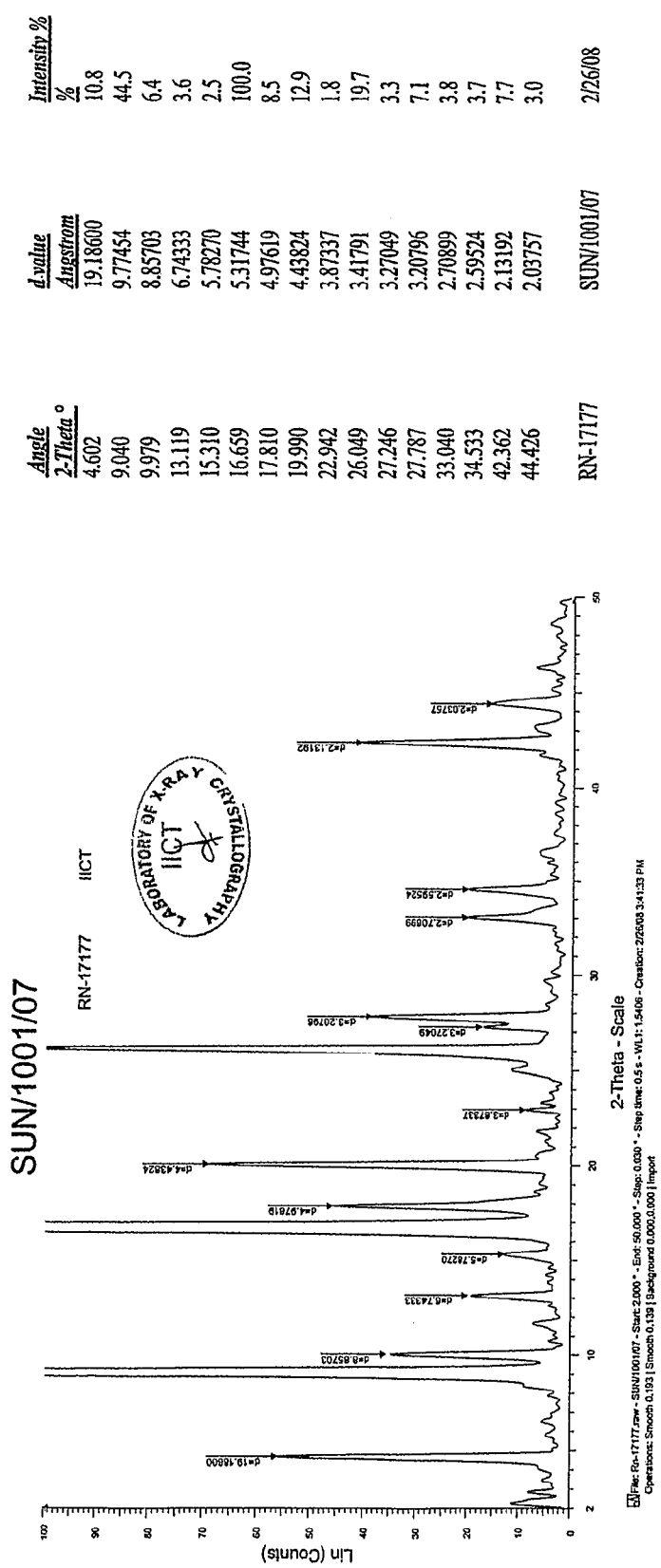
Fig. 1: Powdered X-ray diffraction of Sunitinib base (I) obtained in methanol (Form-A)

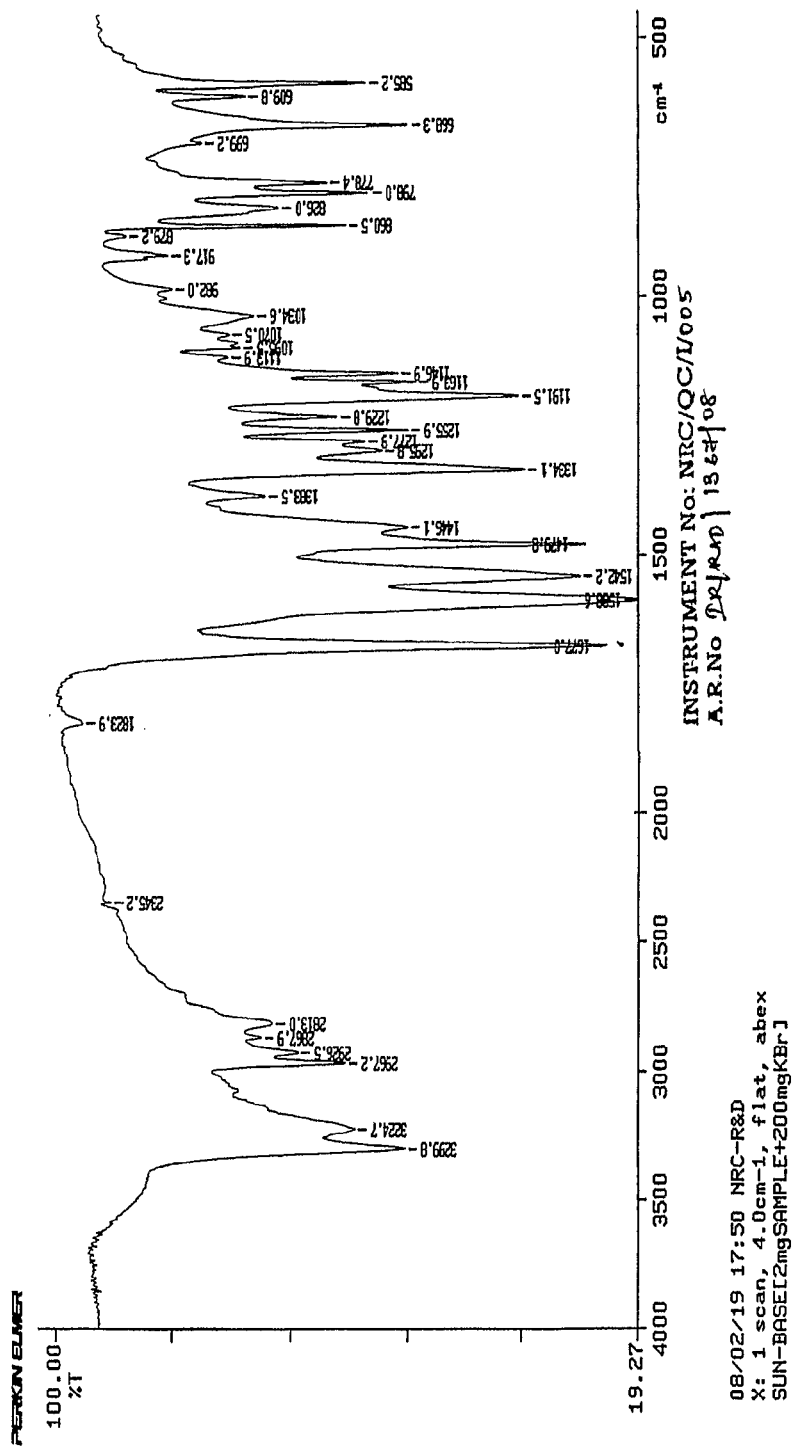
Fig 2: FTIR spectrum of Sunitinib base (I) obtained in methanol (Form-A)

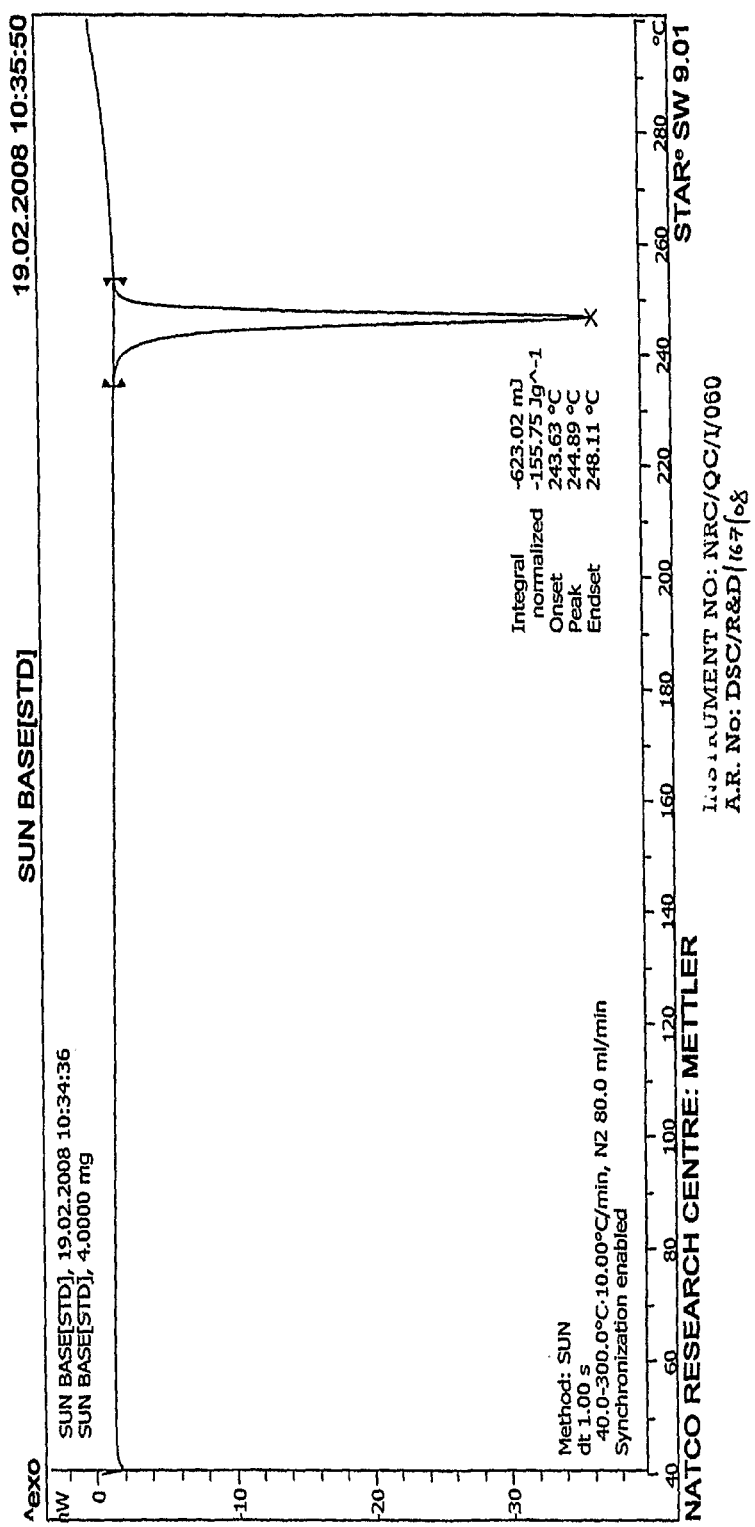
Fig 3: DSC of Sunitinib base (I) obtained in methanol (Form-A)

Fig 4: Powdered X-Ray diffractogram of Sunitinib base (I) obtained in n-hexane (Form-B)

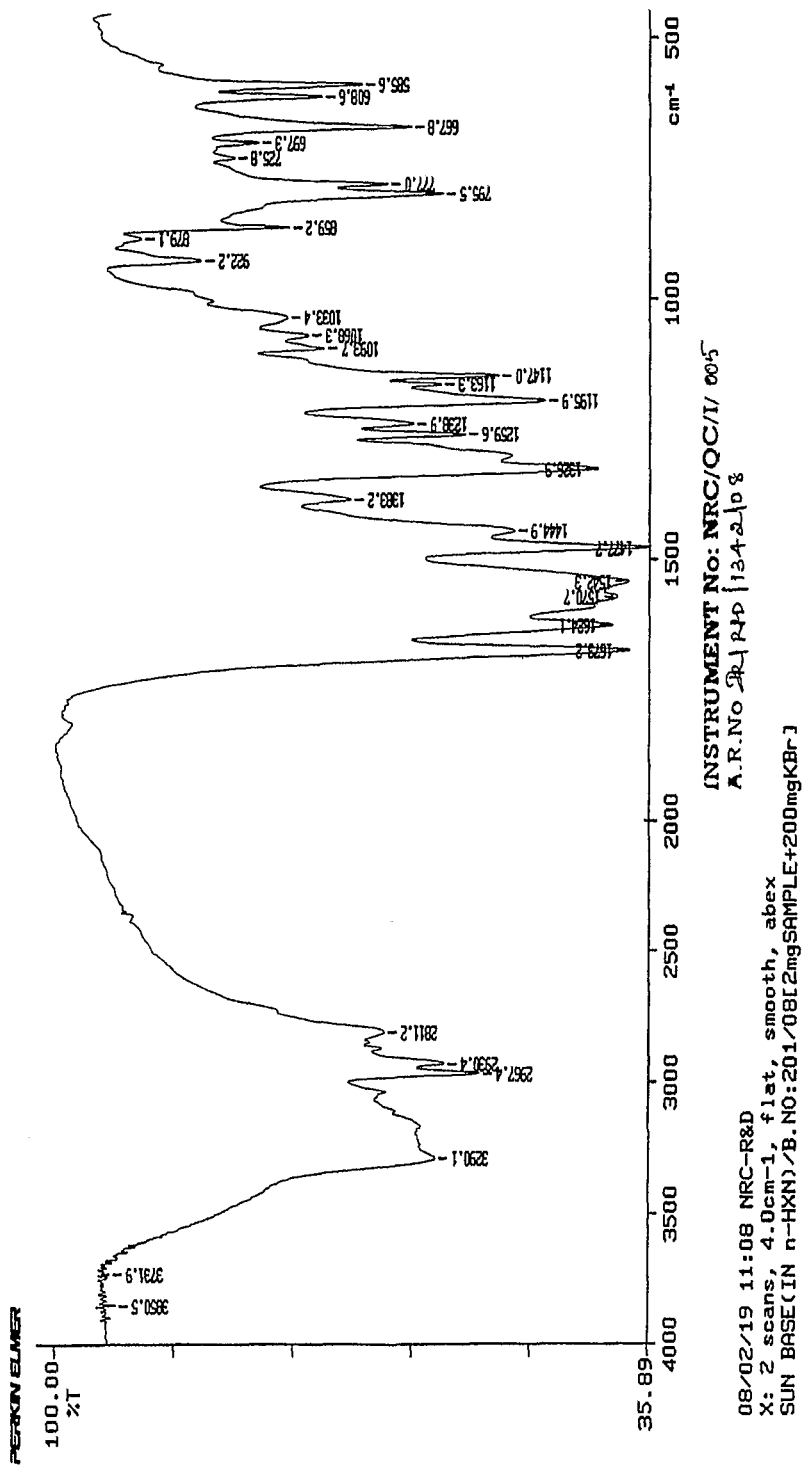
Fig 5: FTIR spectrum of Sunitinib base (I) obtained in n-hexane (Form-B)

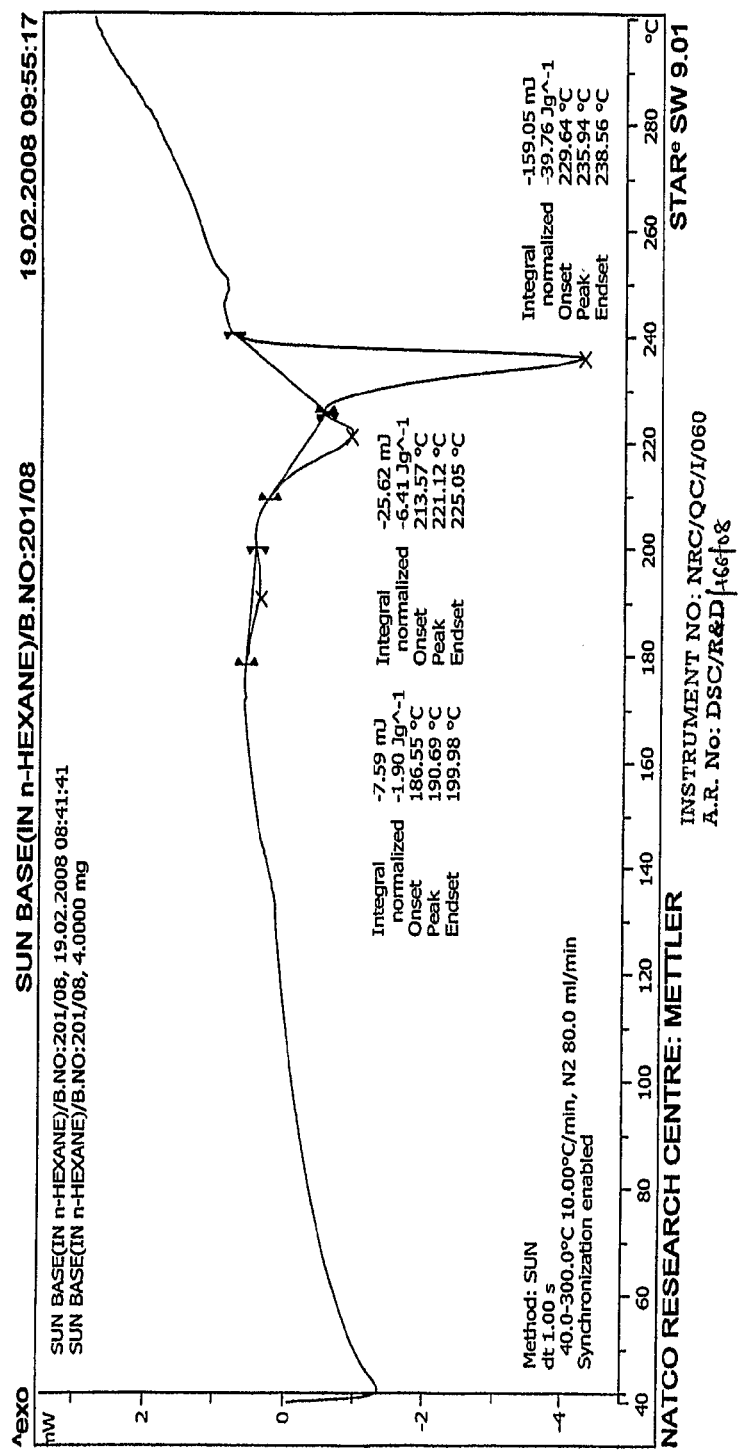
Fig 6: DSC of Sunitinib base (I) obtained in n-hexane (Form-B)

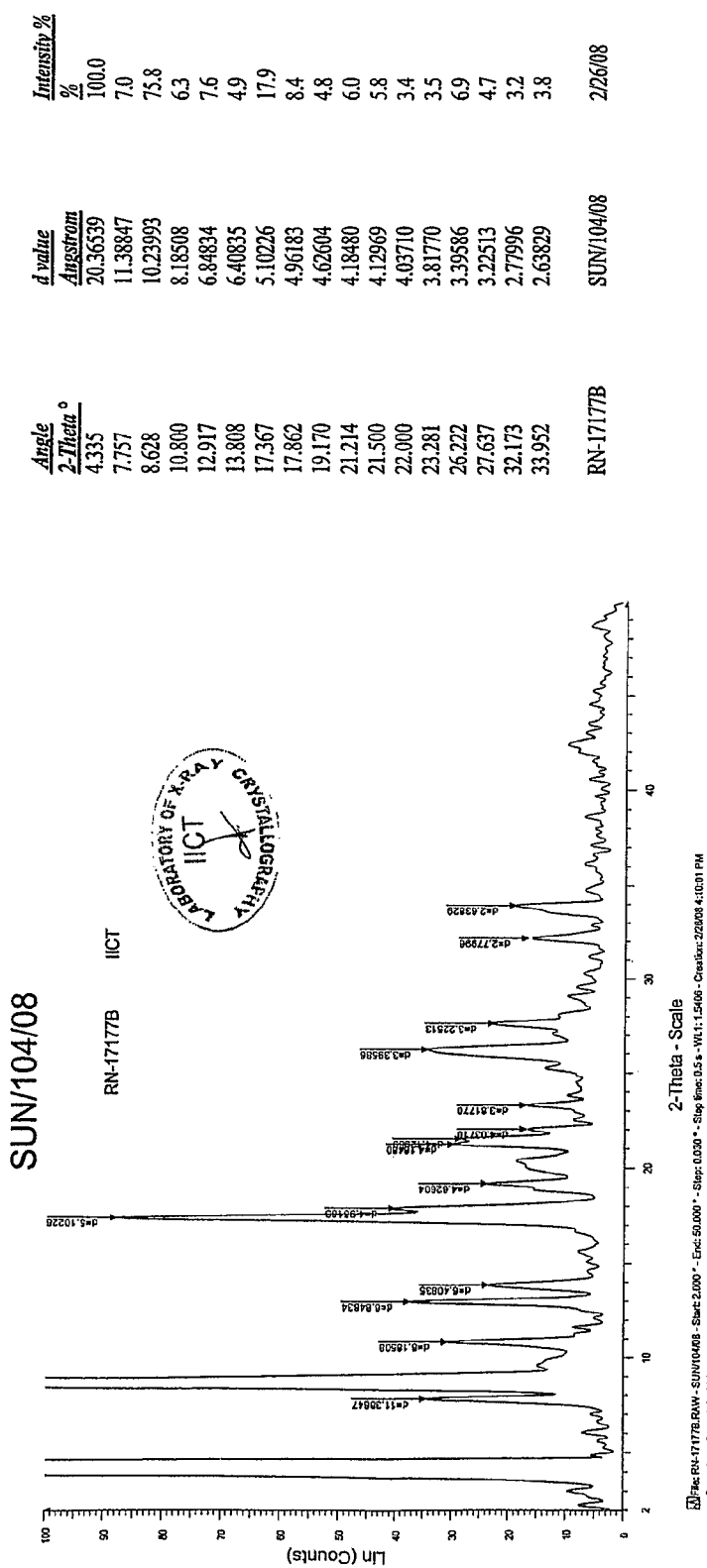
Fig 7: Powdered X-Ray diffractogram of Sunitinib base (I) obtained in cyclohexane (Form-C)

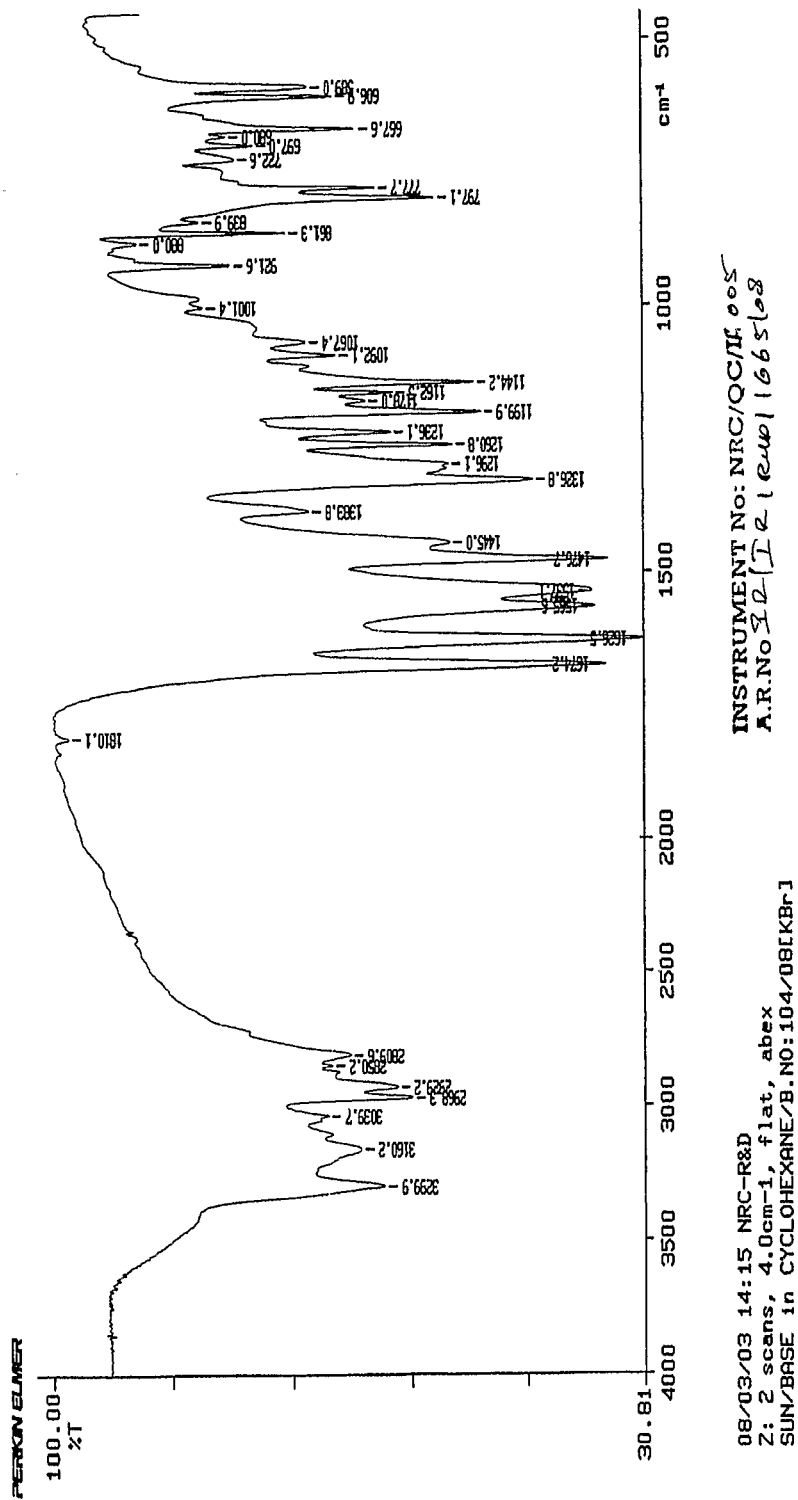
Fig 8: FTIR spectrum of Sunitinib base (I) obtained in cyclohexane (Form-C)

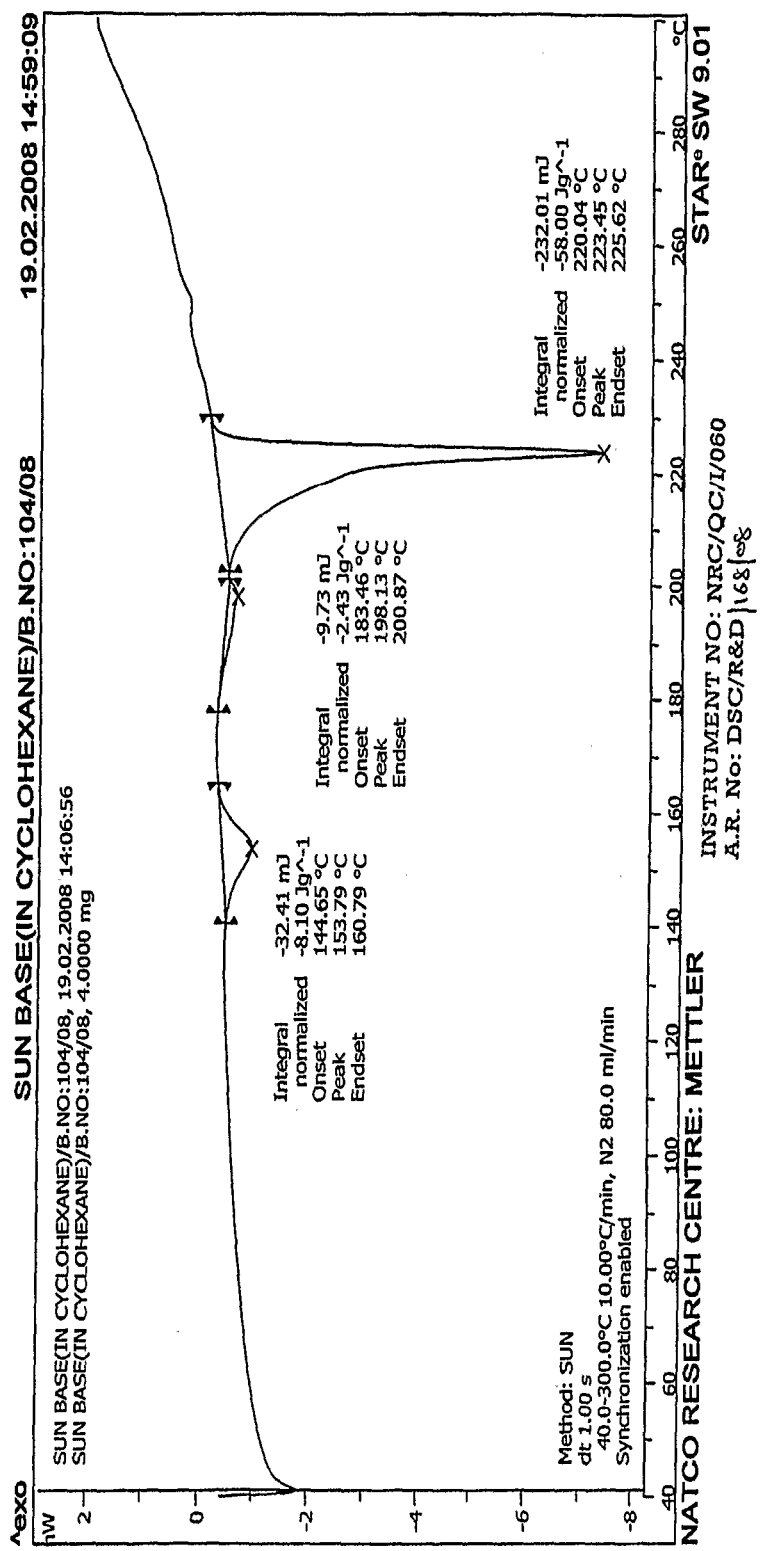
Fig 9: DSC of Sunitinib base (I) obtained in cyclohexane (Form-C)

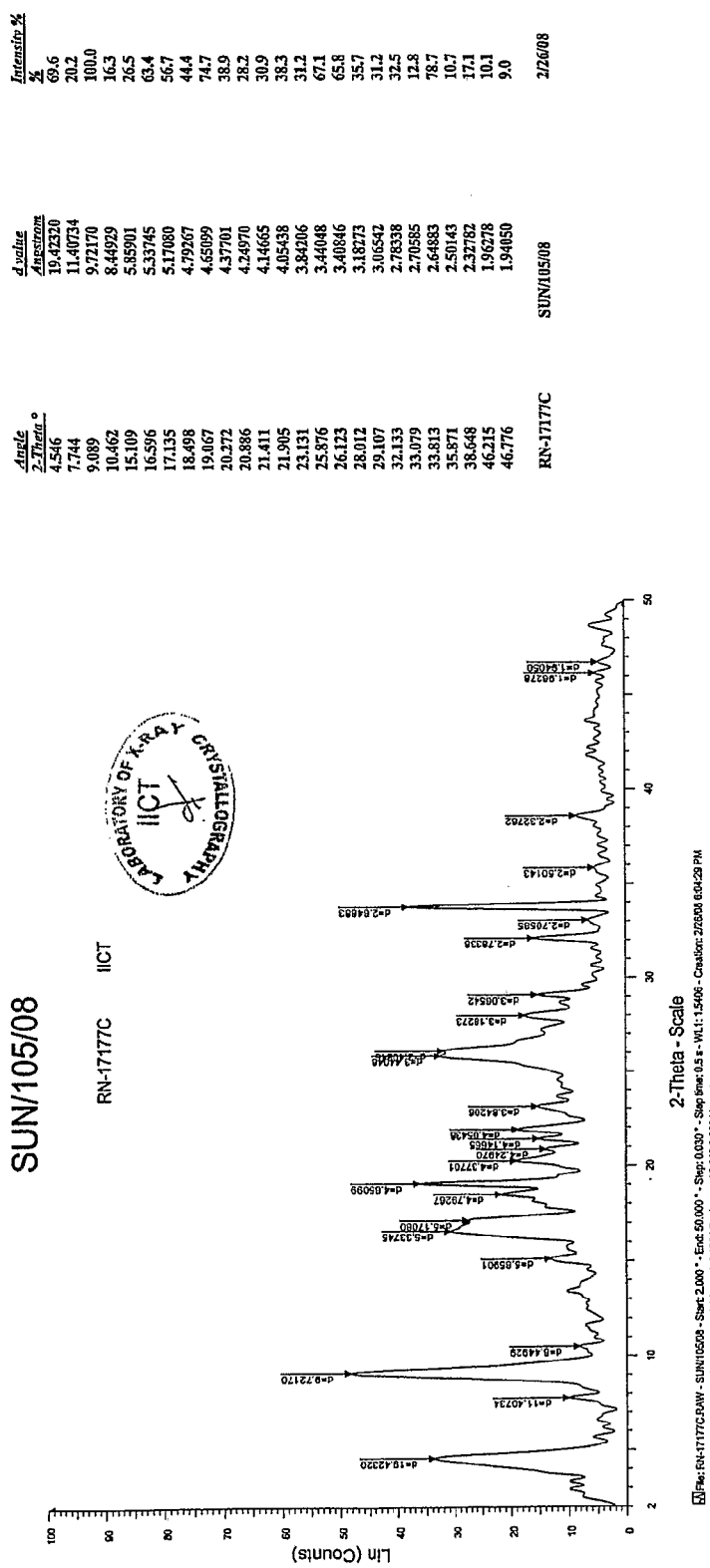
Fig 10: Powdered X-Ray diffractogram of Sunitinib base (I) obtained in toluene (Form-D)

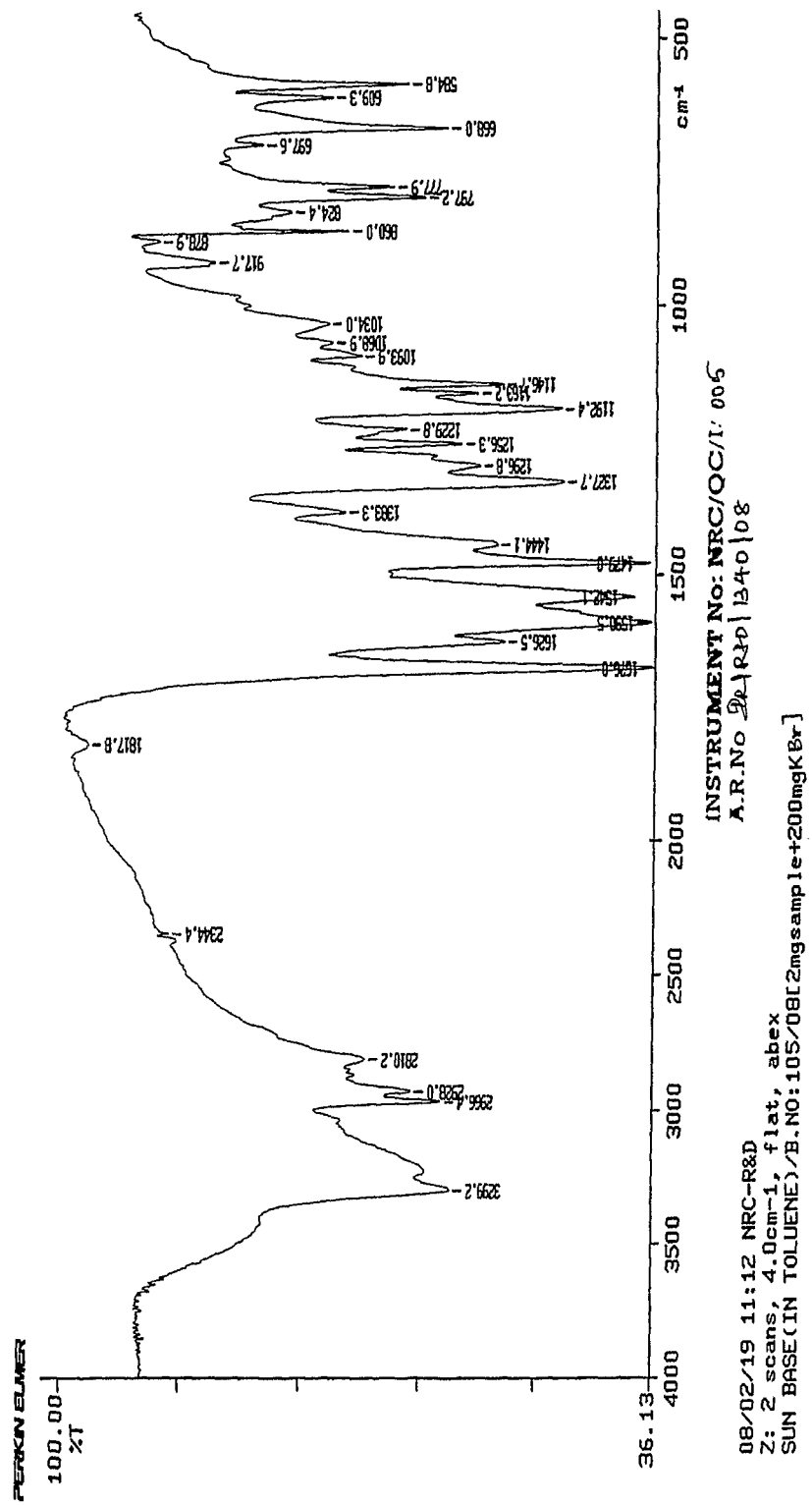
Fig 11: FTIR spectrum of Sunitinib base (I) obtained in toluene (Form-D)

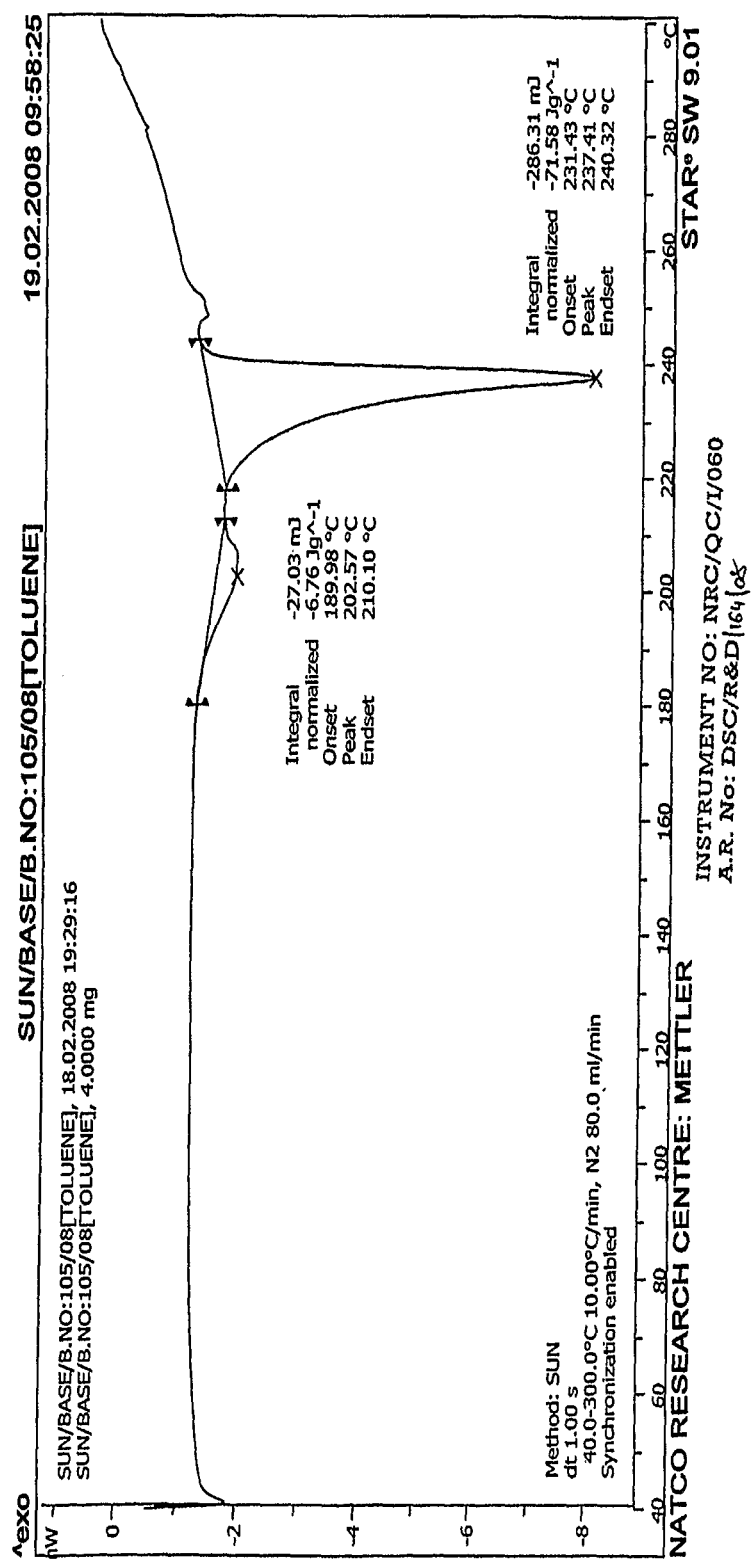
Fig 12: DSC of Sunitinib base (I) obtained in toluene (Form-D)

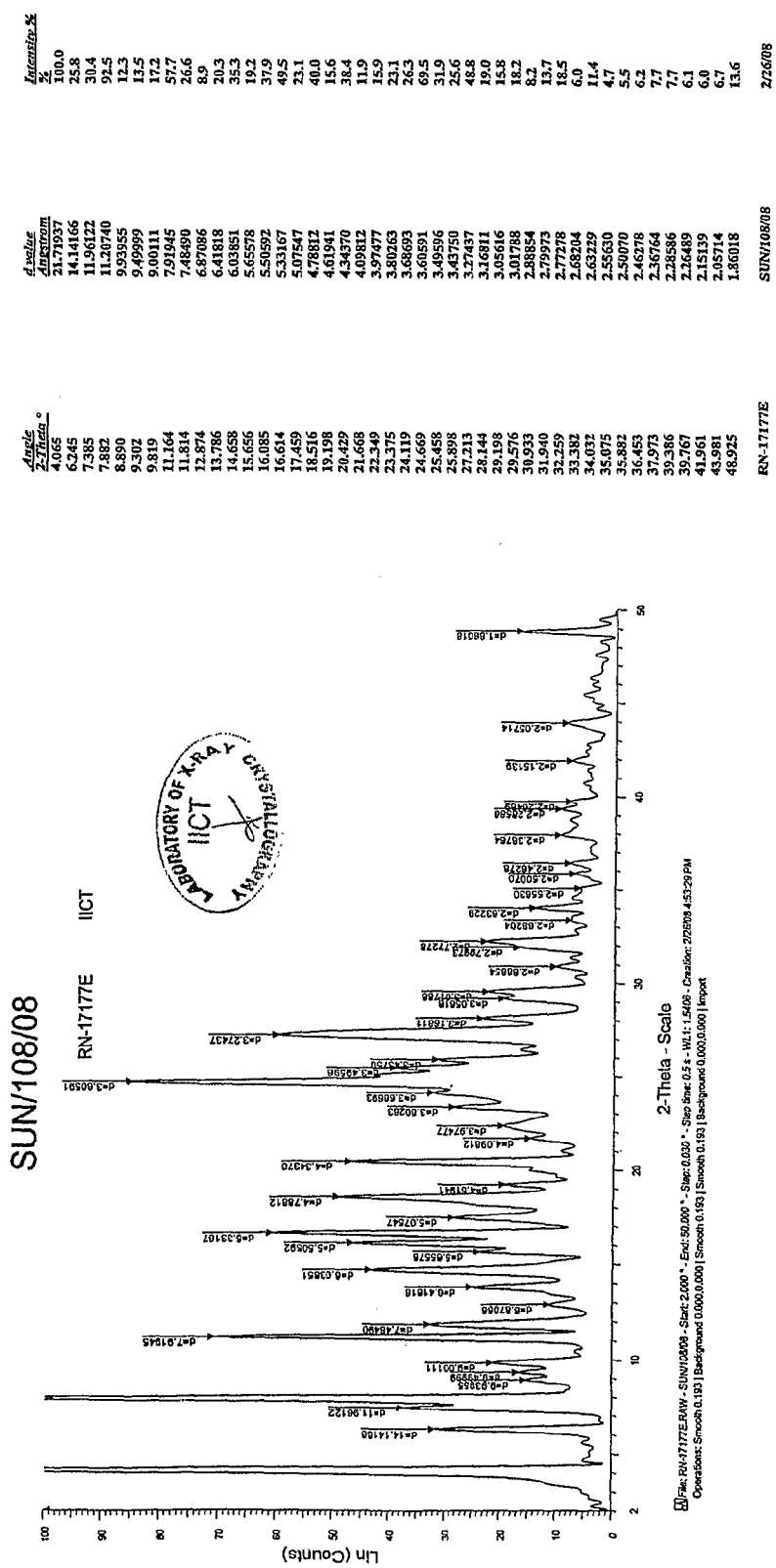
Fig 13: Powdered X-Ray diffractogram of Sunitinib base (I) obtained in isopropyl acetate (Form-E)

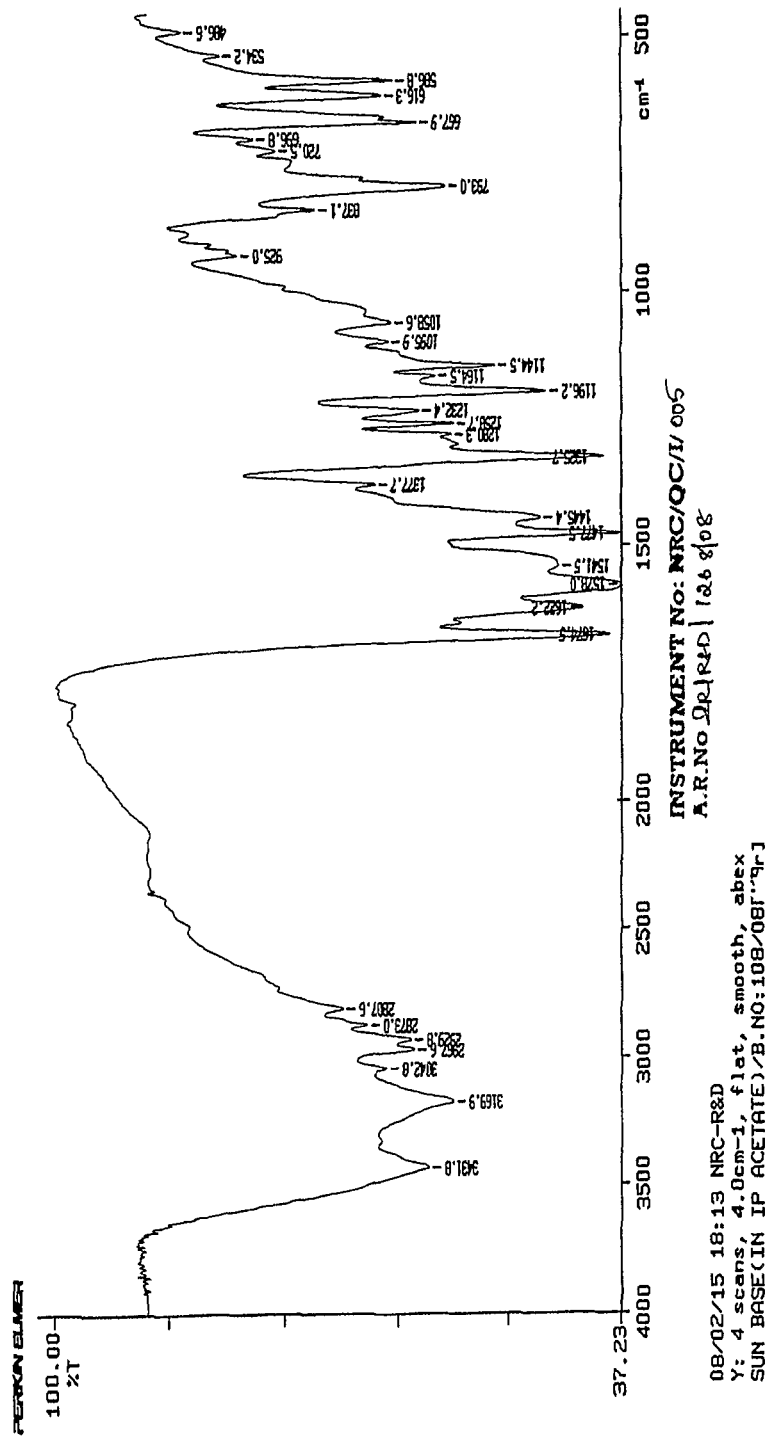
Fig 14: FTIR spectrum of Sunitinib base (I) obtained in isopropyl acetate (Form-E)

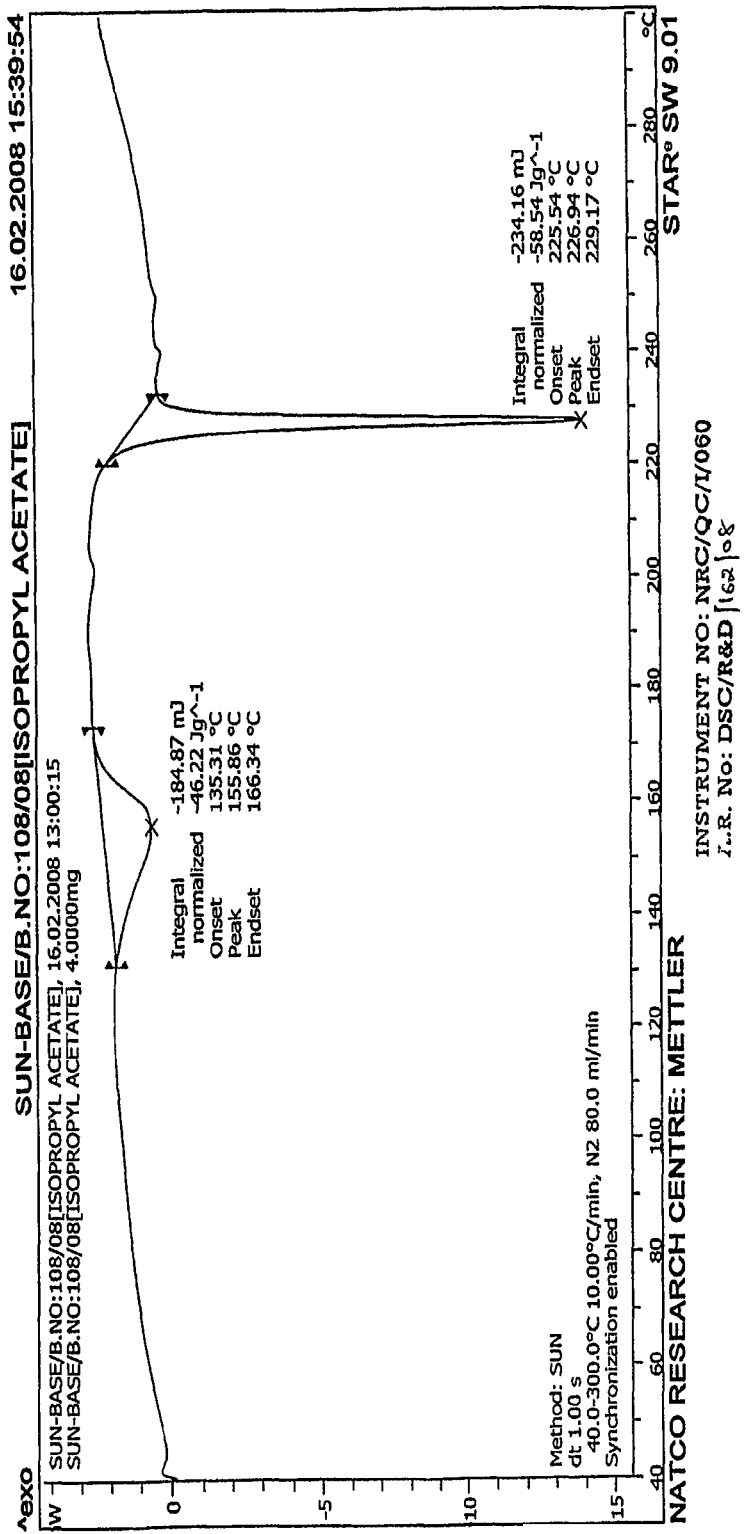
Fig 15: DSC of Sunitinib base (I) obtained in isopropyl acetate (Form-E)

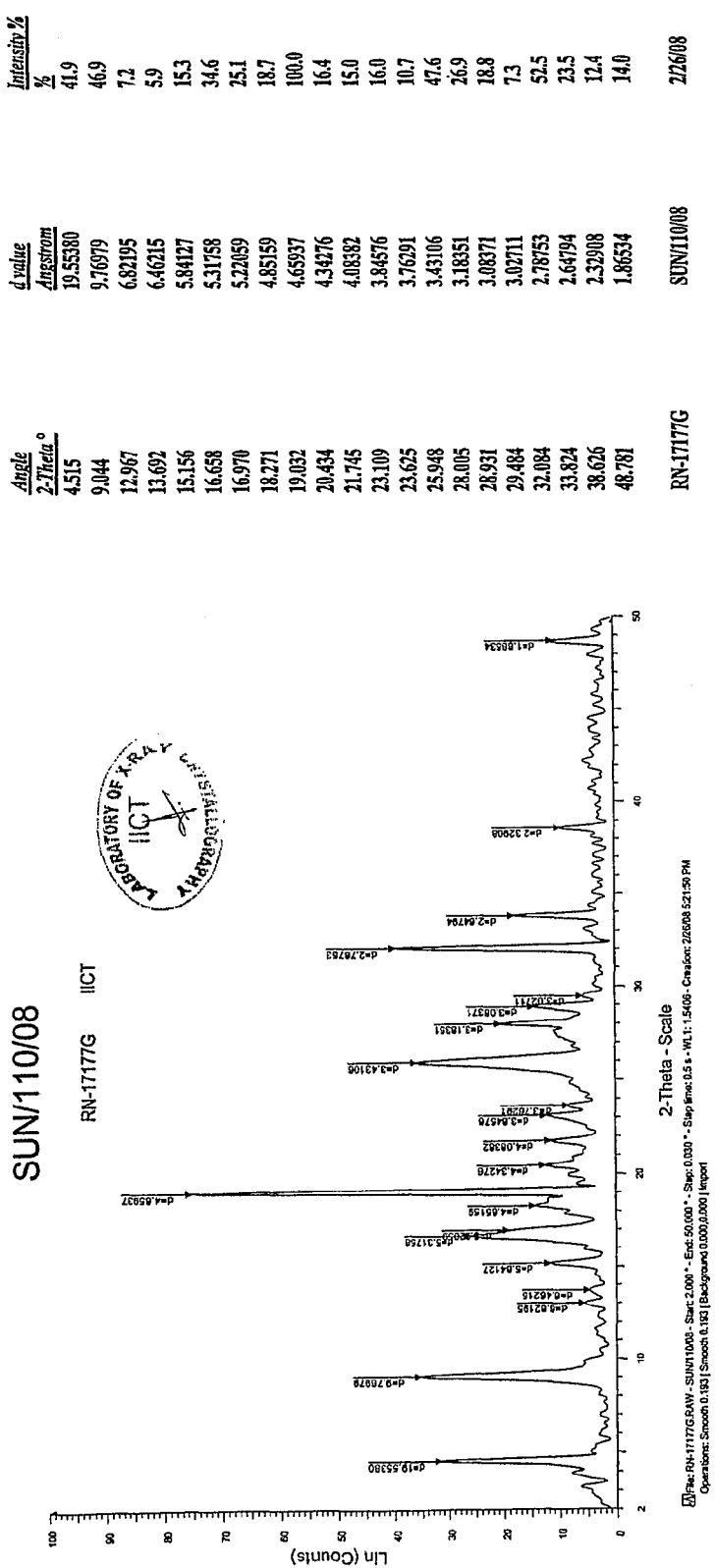
Fig 16: Powdered X-Ray diffractogram of Sunitinib base (I) obtained in tetrahydrofuran (Form-F)

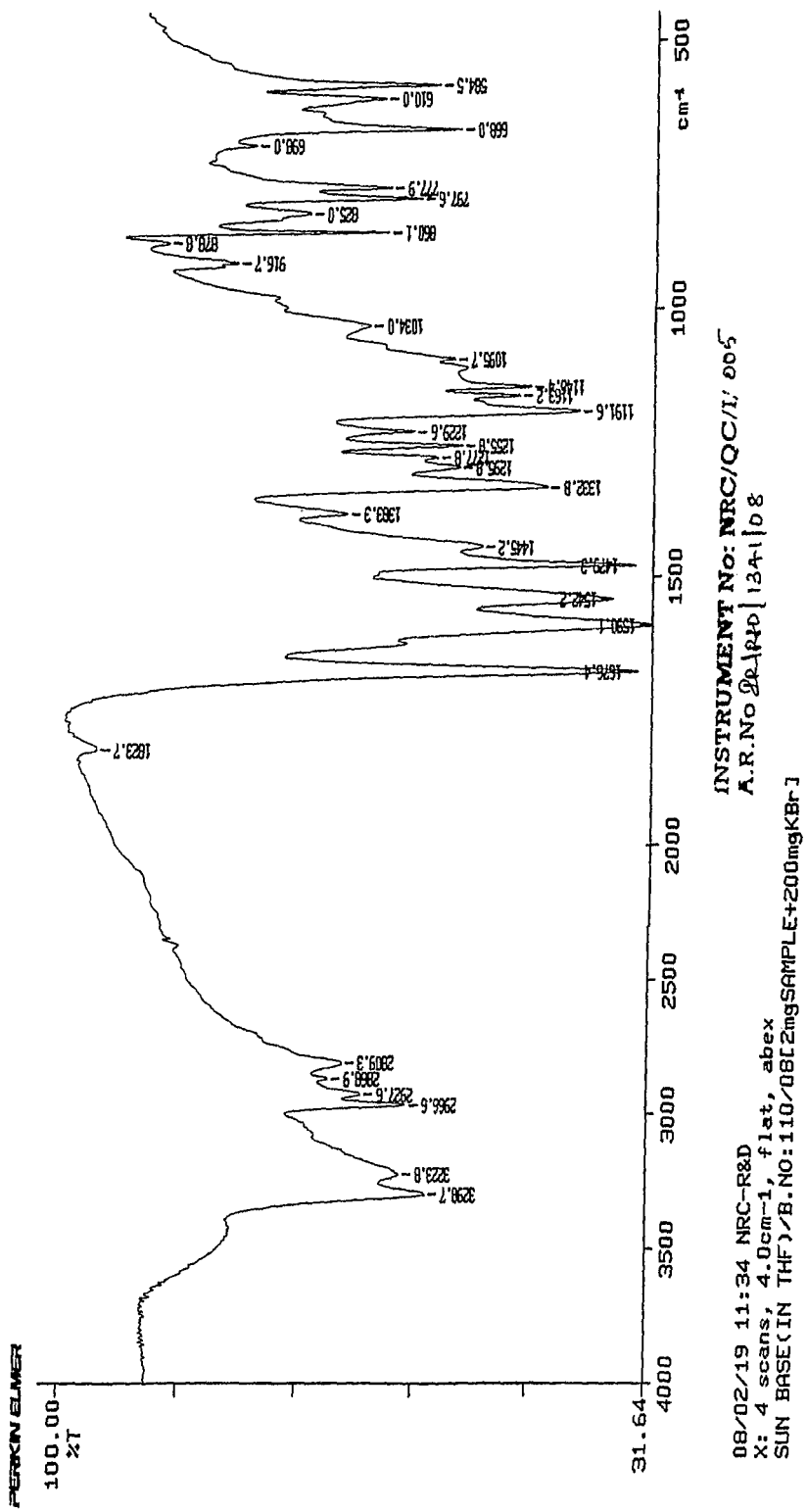
Fig 17: FTIR spectrum of Sunitinib base (I) obtained in tetrahydrofuran (Form-F)

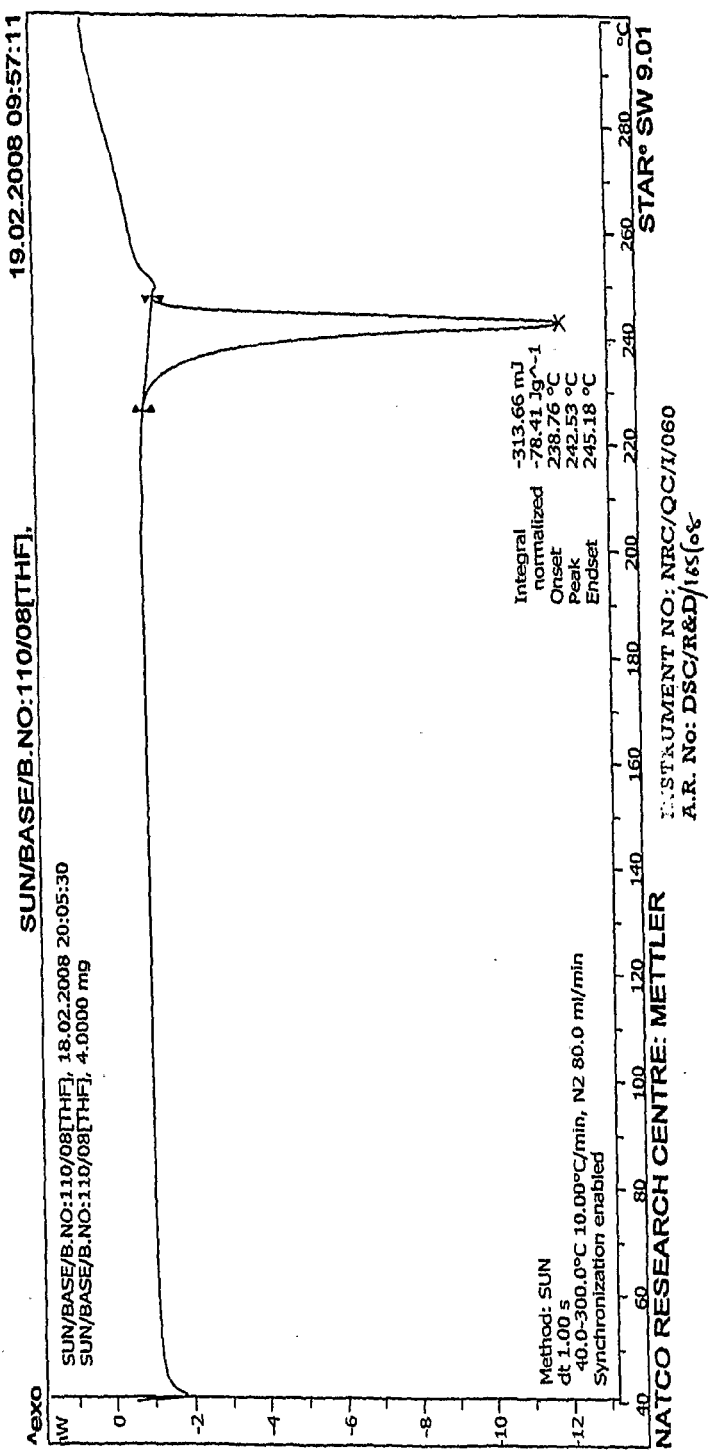
Fig 18: DSC of Sunitinib base (I) obtained in tetrahydrofuran (Form-F)

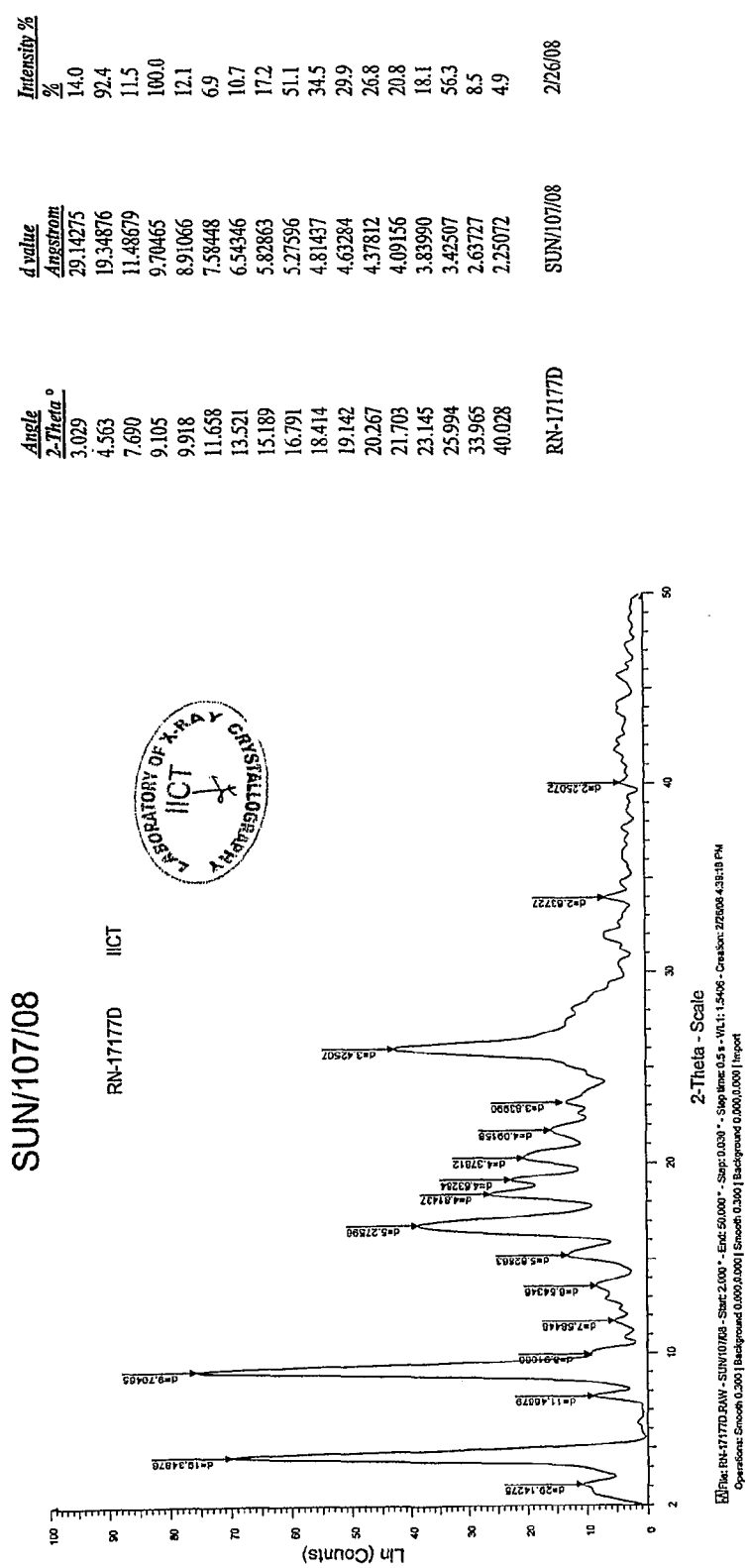
Fig 19: Powdered X-Ray diffractogram of Sunitinib base (I) obtained in methyl tert. butyl ether (Form-G)

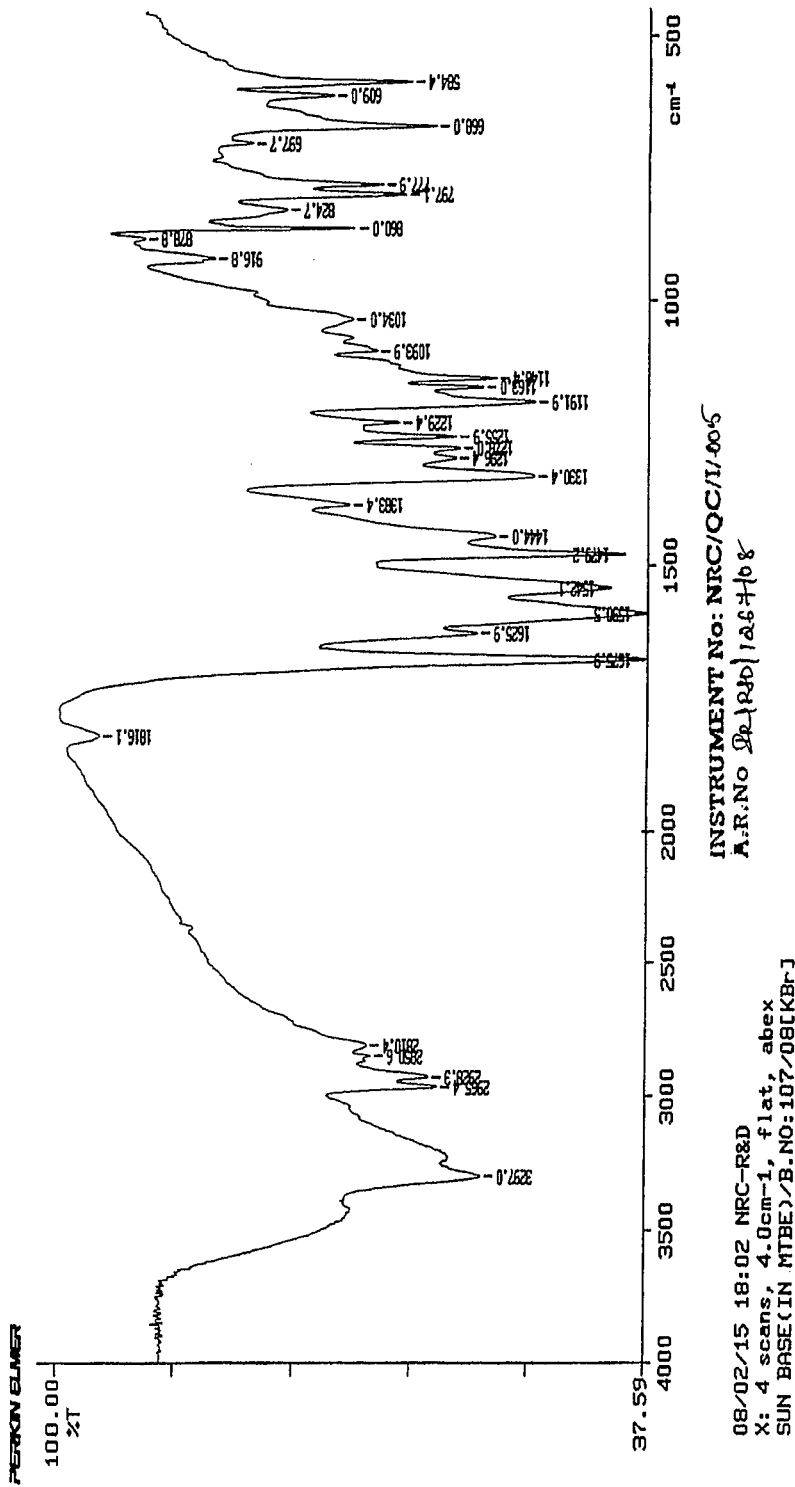
Fig 20: FTIR spectrum of Sunitinib base (I) obtained in methyl tert. butyl ether (Form-G)

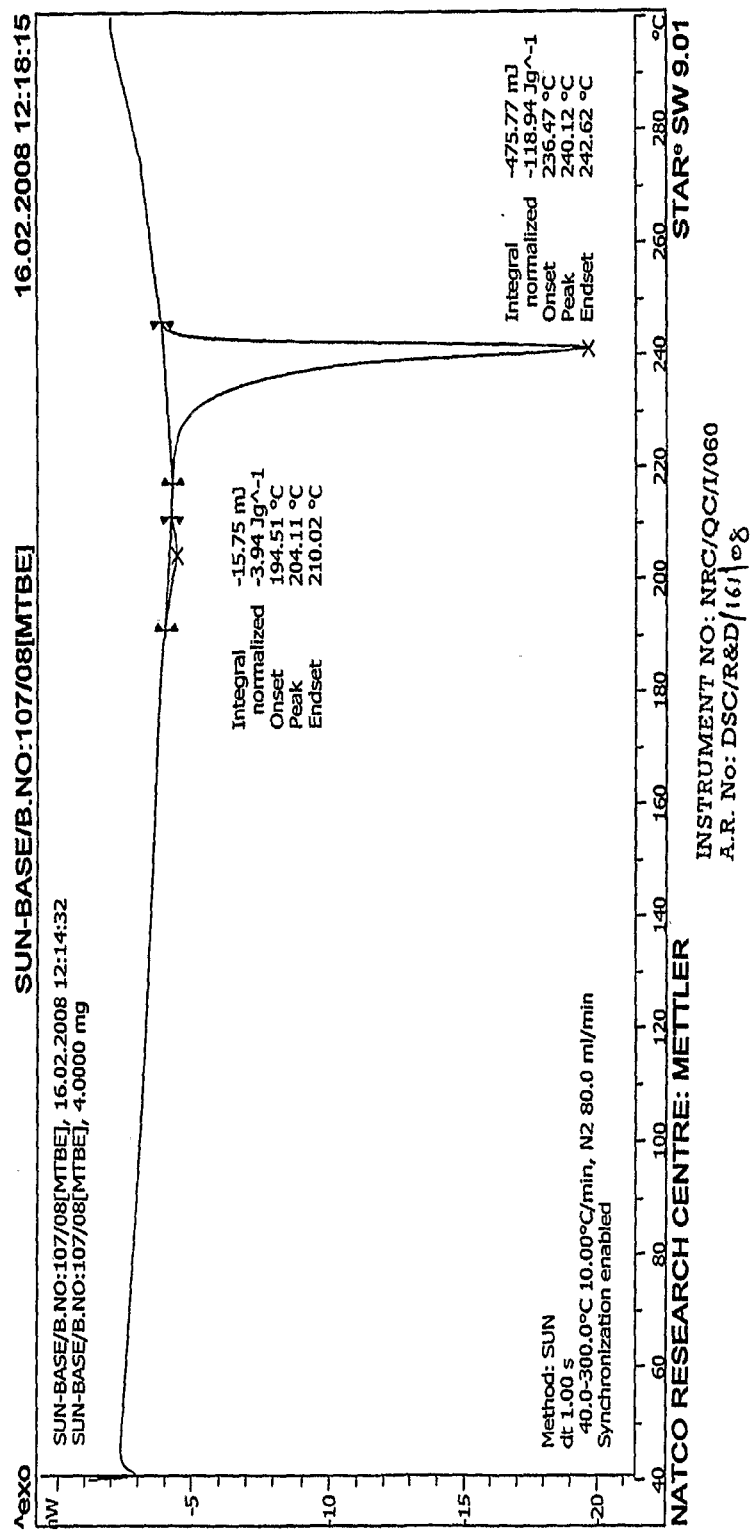
Fig 21: DSC of Sunitinib base (I) obtained in methyl tert. butyl ether (Form-G)

POLYMORPHIC FORMS OF SUNITINIB BASE

FIELD OF INVENTION

The present invention relates to novel polymorphic forms of N-[2-(diethylamino)ethyl]-5-[(5-fluoro-1,2-dihydro-2-oxo-3H-indol-3-ylidene)methyl-2,4-dimethyl-1H-pyrrole-3-carboxamide-Sunitinib base (I). The present invention also relates to methods of preparing such polymorphic crystals.

Sunitinib is a small molecule inhibitor of multiple receptor kinases involved in cancer, including vascular endothelial growth factor receptors, platelet derived growth factor receptors and the KIT receptor. It has been recently approved by the US FDA for the treatment of Gastro Intestinal Stromal Tumors (GIST) and Advanced Renal Cell Carcinoma (RCC).

Studies revealed that Sunitinib malate (SUTENT®) is an oral, multi-targeted tyrosine kinase inhibitor (TK1) that targets and blocks the signaling pathways of multiple selected receptor tyrosine kinases (RTKs). SUTENT® is administered via oral route.

Sunitinib exists as yellow to orange powder. Sunitinib is a non-hygroscopic substance and has no chiral center, however the final substance is optically active due to malate part of the molecule.

BACKGROUND OF THE INVENTION

Sunitinib base is having the chemical name N-[2-(diethylamino)ethyl]-5-[(5-fluoro-1,2-dihydro-2-oxo-3H-indol-3-ylidene)methyl-2,4-dimethyl-1H-pyrrole-3-carboxamide is also known as SU11248 and similar pyrrole derivatives are first disclosed in WO 0160814 (2001).

In the above said patent, the manufacturing process for Sunitinib is described as shown in Scheme-1 below.

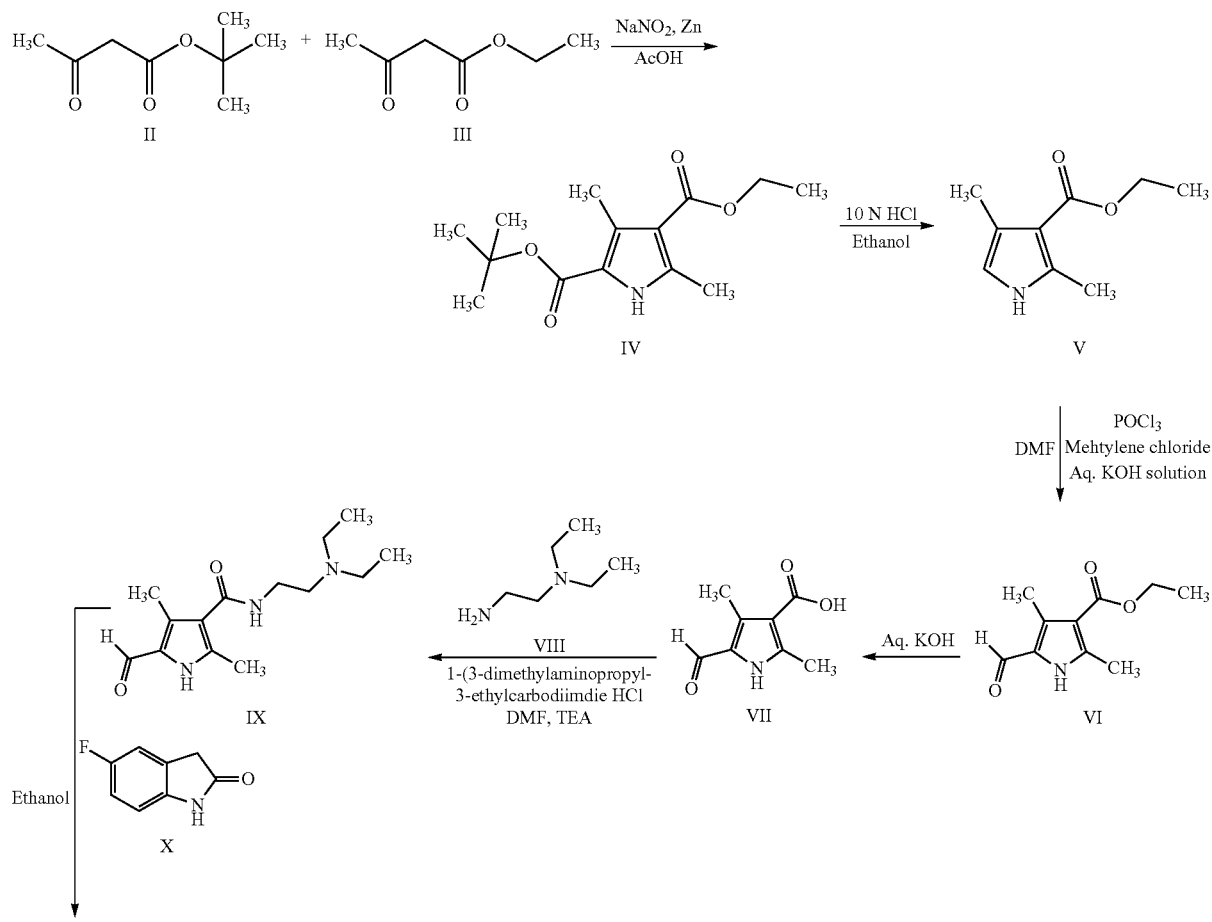

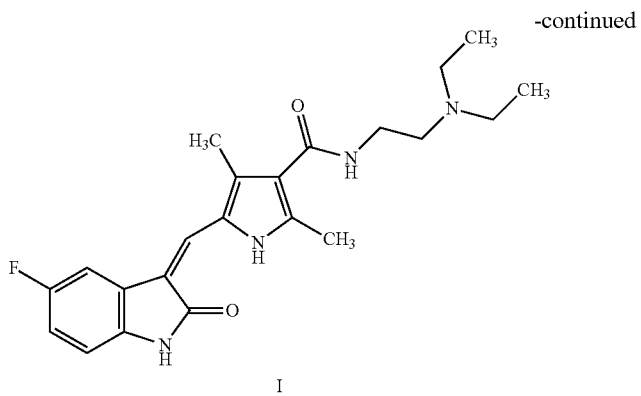

I

According to the above patent:

Tertiary butylacetoacetate (II) and ethyl acetatoacetate (III) were reacted by a well-known Knorr-pyrrole synthesis (Org. Synth., Coll. Vol. II, p 202) using sodium nitrite, zinc and acetic acid to get the diester pyrrole derivative (IV).

Later it is selectively decarboxylated in the presence of aqueous HCl to get half-ester pyrrole derivative (V).

The compound (V) is then formylated by a known synthetic methodology using DMF-POCl$_3$ complex to get the formylated ester derivative (VI).

The half-ester derivative (VI) is selectively hydrolyzed to get a carboxylic acid derivative (VII).

The carboxylic acid derivative (VII) is then selectively converted to amide (IX) using 2-(Diethylamino ethylamine (VIII) in the presence of 1-(3-dimethylaminopropyl-3-ethyl-carbodiimide HCl.

Finally the formyl derivative (IX) is coupled with 5-Fluoro-2-oxindole (X) by Knoevenagel method using pyrrolidine as a catalyst to get Sunitinib base (I). The product was characterized by $^1$H NMR and Mass spectral analysis.

However, the information regarding the solid state characteristics like powder XRD, DSC, IR data or specific crystal forms of N-[2-(diethylamino)ethyl]-5-[(5-fluoro-1,2-dihydro-2-oxo-3H-indol-3-ylidene)methyl-2,4-dimethyl-1H-pyrrole-3-carboxamide-Sunitinib base (I) are not disclosed in the above mentioned patent (WO 01/60814).

A study of the solid state properties of this important anti-cancer entity will be extremely useful from the therapeutic and pharmaceutical point of view. Hence we have taken up a detailed investigation of these aspects.

In the current scenario demanding high quality standards of drug substances and drug products, physical characteristics (like powdered XRD, DSC and IR) play an important role in pharmaceutical industry.

Due to poor solubility nature of Sunitinib base in ethanol or methanol, very large volumes of solvent is required to crystallize Sunitinib base. Hence a better process for preparation of high purity of Sunitinib base directly obtainable from the reaction mixture is highly desirable. In that direction a detailed study was taken-up.

During our experimental work on the reactivity of Sunitinib base in various solvents, surprisingly a wide variety of novel polymorphic forms of the said base were discovered. These novel forms are found to be stable, reproducible, and suitable for conversion to pharmaceutically acceptable salt preparations. Also, surprisingly the condensation of formyl derivative (IX) with 5-Fluoro-2-oxindole (X) is found to proceed even in the absence of a catalyst.

However, certain basic and acidic catalysts are found to hasten the reaction and improve the yields. These catalysts include inorganic bases like ammonia, alkali metal or alkaline earth hydroxides, carbonates, phosphates, bicarbonates and alkali metal hydroxides viz sodium hydroxide, potassium hydroxide or alkaline earth metal hydroxides viz calcium hydroxide, magnesium hydroxide or barium hydroxide, methanolic or ethanolic ammonia, quaternary ammonium compounds like tetra butyl ammonium hydroxide, benzyltrimethyl ammonium hydroxide, silica gel, sodium acetate, ammonium acetate or Lewis acids like Boron trifluoride etherate and organic bases like piperidine, piperazine, pyrrolidine, sodium ethoxide, sodium methoxide, para toluene sulfonic acid (PTSA) are found to hasten the reaction and improve the yields.

OBJECTIVES OF THE PRESENT INVENTION

The main objective of the present invention is to provide a detailed process/crystallization conditions for the synthesis of Sunitinib base (I).

Accordingly, another objective of the present invention is to provide complete physical characterization like XRD, DSC, IR of Sunitinib base (I).

Accordingly, yet another objective of the present invention is to provide physical characterization data like XRD, IR, and DSC for Sunitinib base (I) obtained in methanol.

Accordingly, yet another objective of the present invention is to provide physical characterization data like XRD, IR, DSC for Sunitinib base (I) obtained in n-hexane.

Accordingly, yet another objective of the present invention is to provide physical characterization data like XRD, IR, DSC for Sunitinib base (I) obtained in cyclohexane.

Accordingly, yet another objective of the present invention is to provide physical characterization data like XRD, IR, DSC for Sunitinib base (I) obtained in toluene.

Accordingly, yet another objective of the present invention is to provide physical characterization data like XRD, IR, DSC for Sunitinib base (I) obtained in isopropyl acetate.

Accordingly, yet another objective of the present invention is to provide physical characterization data like XRD, IR, DSC for Sunitinib base (I) obtained in tetrahydrofuran.

Accordingly, yet another objective of the present invention is to provide physical characterization data like XRD, IR, DSC for Sunitinib base (I) obtained in methyl tertiary butyl ether.

BRIEF DESCRIPTION OF THE FIGURES

FIG. 1: Powdered X-ray diffraction of Sunitinib base (I) obtained in methanol (Form-A)

FIG. 2: FTIR spectrum of Sunitinib base (I) obtained in methanol (Form-A)

FIG. 3: DSC of Sunitinib base (I) obtained in methanol (Form-A)

FIG. 4: Powdered X-Ray diffractogram of Sunitinib base (I) obtained in n-hexane (Form-B)

FIG. 5: FTIR spectrum of Sunitinib base (I) obtained in n-hexane (Form-B)

FIG. 6: DSC of Sunitinib base (I) obtained in n-hexane (Form-B)

FIG. 7: Powdered X-Ray diffractogram of Sunitinib base (I) obtained in cyclohexane (Form-C)

FIG. 8: FTIR spectrum of Sunitinib base (I) obtained in cyclohexane (Form-C)

FIG. 9: DSC of Sunitinib base (I) obtained in cyclohexane (Form-C)

FIG. 10: Powdered X-Ray diffractogram of Sunitinib base (I) obtained in toluene (Form-D)

FIG. 11: FTIR spectrum of Sunitinib base (I) obtained in toluene (Form-D)

FIG. 12: DSC of Sunitinib base (I) obtained in toluene (Form-D)

FIG. 13: Powdered X-Ray diffractogram of Sunitinib base (I) obtained in isopropyl acetate (Form-E)

FIG. 14: FTIR spectrum of Sunitinib base (I) obtained in isopropyl acetate (Form-E)

FIG. 15: DSC of Sunitinib base (I) obtained in isopropyl acetate (Form-E)

FIG. 16: Powdered X-Ray diffractogram of Sunitinib base (I) obtained in tetrahydrofuran (Form-F)

FIG. 17: FTIR spectrum of Sunitinib base (I) obtained in tetrahydrofuran (Form-F)

FIG. 18: DSC of Sunitinib base (I) obtained in tetrahydrofuran (Form-F)

FIG. 19: Powdered X-Ray diffractogram of Sunitinib base (I) obtained in methyl tert. butyl ether (Form-G)

FIG. 20: FTIR spectrum of Sunitinib base (I) obtained in methyl tert. butyl ether (Form-G)

FIG. 21: DSC of Sunitinib base (I) obtained in methyl tert. butyl ether (Form-G)

SUMMARY OF THE PRESENT INVENTION

In one aspect, the present invention provides a crystalline form (Form-A) of Sunitinib base also known as N-[2-(diethylamino)ethyl]-5-[(5-fluoro-1,2-dihydro-2-oxo-3H-indol-3-ylidene)methyl-2,4-dimethyl-1H-pyrrole-3-carboxamide (I) obtained in methanol as solvent. The crystal has the following characteristics.

Powder XRD diffraction pattern having 2θ values at 4.6, 9.0, 9.9, 13.1, 15.3, 16.6, 17.8, 19.9, 22.9, 26.0, 27.2, 27.7, 33.0, 34.5, 42.3, 44.4 (FIG. 1)

FTIR $(cm^{-1})$ spectra: 3299.8, 1677.0, 1588.6, 1542.2, 1479.0, 1334.1, 1191.5, 860.5, 798.0, 778.4, 668.3, 585.2 (FIG. 2)

DSC (° C.): Peak Max. 244.9° C. (FIG. 3)

In another aspect, the present invention provides a crystalline form (Form-B) of Sunitinib base obtained in n-hexane as solvent. The crystal has the following characteristics.

Powder XRD diffraction pattern having 2θ values at 3.9, 7.8, 9.1, 10.3, 11.8, 13.7, 15.9, 16.8, 18.0, 19.0, 20.2, 21.3, 21.9, 22.6, 23.7, 24.4, 26.0, 26.8, 28.1, 29.5, 32.1, 32.5, 33.8, 37.4, 43.1 (FIG. 4)

FTIR $(cm^{-1})$ spectra: 3290.1, 1673.2, 1624.1, 1570.7, 1542.3, 1477.7, 1326.9, 1195.9, 795.5, 667.8, 585.6 (FIG. 5)

DSC (° C.): Principal Peak Max. 235.9° C. (FIG. 6)

In another aspect, the present invention provides a crystalline form (Form-C) of Sunitinib base obtained in cyclohexane as solvent. The crystal has the following characteristics.

Powder XRD diffraction pattern having 2θ values at 4.3, 7.7, 8.6, 10.8, 12.9, 13.8, 17.3, 17.8, 19.1, 21.2, 21.5, 22.0, 23.2, 26.2, 27.6, 32.1, 33.9 (FIG. 7)

FTIR $(cm^{-1})$ spectra: 3299.9, 1674.2, 1626.5, 1565.6, 1537.1, 1476.7, 1326.8, 1199.9, 1144.2, 797.1, 667.6, 606.9, 589.0 (FIG. 8)

DSC (° C.): Principal Peak Max. 223.5° C. (FIG. 9)

In another aspect, the present invention provides a crystalline form (Form-D) of Sunitinib base obtained in toluene as solvent. The crystal has the following characteristics.

Powder XRD diffraction pattern having 2θ values at 4.5, 7.7, 9.0, 10.4, 15.1, 16.5, 17.1, 18.4, 19.0, 20.2, 20.8, 21.4, 21.9, 23.1, 25.8, 26.1, 28.0, 29.1, 32.1, 33.0, 33.8, 35.8, 38.6, 46.2, 46.7 (FIG. 10)

FTIR $(cm^{-1})$ spectra: 3299.2, 1676.0, 1626.5, 1590.5, 1542.1, 1479.0, 1327.7, 1192.4, 860.0, 797.2, 777.9, 668.0, 584.8 (FIG. 11)

DSC (° C.): Principal Peak Max. 237.4° C. (FIG. 12)

In another aspect, the present invention provides a crystalline form (Form-E) of Sunitinib base obtained in isopropyl acetate as solvent. The crystal has the following characteristics.

Powder XRD diffraction pattern having 2θ values at 4.0, 6.2, 7.3, 7.8, 8.8, 9.3, 9.8, 11.1, 11.8, 12.8, 13.7, 14.6, 15.6, 16.0, 16.6, 17.4, 18.5, 19.1, 20.4, 21.6, 22.3, 23.3, 24.1, 24.6, 25.4, 25.8, 27.2, 28.1, 29.1, 29.5, 30.9, 31.9, 32.2, 33.3, 34.0, 35.0, 35.8, 36.4, 37.9, 39.3, 39.7, 41.9, 43.9, 48.9 (FIG. 13)

FTIR $(cm^{-1})$ spectra: 3431.8, 3169.9, 1674.5, 1622.2, 1578.0, 1477.5, 1325.7, 1196.2, 1144.5, 793.0, 667.9, 586.8 (FIG. 14)

DSC (° C.): Principal Peak Max. 226.9° C. (FIG. 15)

In another aspect, the present invention provides a crystalline form (Form-F) of Sunitinib base obtained in tetrahydrofuran as solvent. The crystal has the following characteristics.

Powder XRD diffraction pattern having 2θ values at 4.5, 9.0, 12.9, 13.6, 15.1, 16.6, 16.9, 18.2, 19.0, 20.4, 21.7, 23.1, 23.6, 25.9, 28.0, 28.9, 29.4, 32.0, 33.8, 38.6, 48.7 (FIG. 16)

FTIR $(cm^{-1})$ spectra: 3298.7, 3223.8, 1676.4, 1590.1, 1542.2, 1479.3, 1332.8, 1191.6, 797.6, 668.0, 584.5 (FIG. 17)

DSC (° C.): Peak Max. 242.5° C. (FIG. 18)

In another aspect, the present invention provides a crystalline form (Form-G) of Sunitinib base obtained in methyl tert. butyl ether as solvent. The crystal has the following characteristics.

Powder XRD diffraction pattern having 2θ values at 3.0, 4.5, 7.6, 9.1, 9.9, 11.6, 13.5, 15.1, 16.7, 18.4, 19.1, 20.2, 21.7, 23.1, 25.9, 33.9, 40.0 (FIG. 19)

FTIR $(cm^{-1})$ spectra: 3297.0, 1675.9, 1625.9, 1590.5, 1542.1, 1479.2, 1330.4, 1191.9, 797.1, 668.0, 584.4 (FIG. 20)

DSC (° C.): Principal Peak Max. 240.1° C. (FIG. 21)

DETAILED DESCRIPTION OF THE PRESENT INVENTION

The details of the present invention for the manufacture of Sunitinib base (I) are as follows:

According to the process of the present invention, 5-Formyl-2,4-dimethyl-1H-pyrrole-3-carboxylic acid (2-diethylaminoethyl)-amide (IX) and 5-Fluoro-1,3-dihydro-indol-2-one (X) in alcoholic solvents like methanol, ethanol, isopropyl alcohol or n-butanol are reacted in presence of catalytic amount of pyrrolidine as base at reflux temperature for 2-8 hours. The resultant Sunitinib base is again triturated with the same solvent at reflux temperature for 1-2 hours and isolated at a temperature ranging from 20-45° C., preferably at 25-35° and most preferably at 25-30° C. and dried at 60° C. for 5-20 hours to get Sunitinib base (I) as orange crystalline solid. This synthetic procedure for the manufacture of Sunitinib base is adopted from WO 01/60814.

Accordingly, the present invention provides a complete physical characteristic data (like Powdered X-Ray diffraction, FTIR, and DSC) for Sunitinib base obtained in alcoholic solvents like methanol, ethanol, isopropyl alcohol or n-butanol Accordingly, the present invention provides the crystalline Form-A obtained in alcoholic solvents like methanol, ethanol, isopropyl alcohol or n-butanol.

According to the process of the present invention, 5-Formyl-2,4-dimethyl-1H-pyrrole-3-carboxylic acid (2-diethylaminoethyl)-amide (IX) and 5-Fluoro-1,3-dihydro-indol-2-one (X) in non-polar aliphatic hydrocarbons solvents like n-hexane, n-heptane, n-octane, n-nonane or n-decane are reacted in presence of catalytic amount of pyrrolidine as base at reflux temperature for 6-12 hours. The resultant Sunitinib base is again triturated with the same solvent at reflux temperature for 1-2 hours and isolated at a temperature ranging from 20-45° C., preferably at 25-35° and most preferably at 25-30° C. and dried at 60° C. for 5-20 hours to get Sunitinib base (I) as orange crystalline solid.

Accordingly, the present invention provides a complete physical characterization data (like Powdered X-Ray diffraction, FTIR, and DSC) for Sunitinib base obtained in non-polar aliphatic hydrocarbons solvent like n-hexane, n-heptane, n-octane, n-nonane or n-decane.

Accordingly, the present invention provides the crystalline Form-B obtained in non-polar aliphatic hydrocarbon solvent like n-hexane, n-heptane, n-octane, n-nonane or n-decane.

According to the process of the present invention, 5-Formyl-2,4-dimethyl-1H-pyrrole-3-carboxylic acid (2-diethylaminoethyl)-amide (IX) and 5-Fluoro-1,3-dihydro-indol-2-one (X) in non-polar alicyclic hydrocarbon solvents like cyclopentane, cyclohexane or cycloheptane are reacted in presence of catalytic amount of pyrrolidine as base at reflux temperature for 1-6 hours. The resultant Sunitinib base is again triturated with the same solvent at reflux temperature for 1-2 hours and isolated at a temperature ranging from 20-45° C., preferably at 25-35° and most preferably at 25-30° C. and dried at 60° C. for 5-20 hours to get Sunitinib base (I) as orange crystalline solid.

Accordingly, the present invention provides a complete physical characterization data (like Powdered X-Ray diffraction, FTIR, and DSC) for Sunitinib base obtained in non-polar alicyclic hydrocarbon solvent like cyclopentane, cyclohexane or cycloheptane.

Accordingly, the present invention provides the crystalline Form-C obtained in non-polar alicyclic hydrocarbon solvent like cyclopentane, cyclohexane or cycloheptane. According to the process of the present invention, 5-Formyl-2,4-dimethyl-1H-pyrrole-3-carboxylic acid (2-diethylaminoethyl)-amide (IX) and 5-Fluoro-1,3-dihydro-indol-2-one (X) in aromatic hydrocarbon solvents like benzene or toluene are reacted in presence of catalytic amount of pyrrolidine as base at 80-85° C. for 3-9 hours. The resultant Sunitinib base is again triturated with the same solvent at 80-85° C. for 1-2 hours and isolated at a temperature ranging from 20-45° C., preferably at 25-35° and most preferably at 25-30° C. and dried at 60° C. for 5-20 hours to get Sunitinib base (I) as orange crystalline solid.

Accordingly, the present invention provides a complete physical characterization data (like Powdered X-Ray diffraction, FTIR, and DSC) for Sunitinib base obtained in aromatic hydrocarbon solvent like benzene or toluene.

Accordingly, the present invention provides the crystalline Form-D obtained in aromatic hydrocarbon solvents like benzene, toluene, xylenes.

According to the process of the present invention, 5-Formyl-2,4-dimethyl-1H-pyrrole-3-carboxylic acid (2-diethylaminoethyl)-amide (IX) and 5-Fluoro-1,3-dihydro-indol-2-one (X) in esters like ethyl acetate, methyl acetate or isopropyl acetate are reacted in presence of catalytic amount of pyrrolidine as base at reflux temperature for 6-15 hours. The resultant Sunitinib base is again triturated with the same solvent at reflux temperature for 1-2 hours and isolated at a temperature ranging from 20-45° C., preferably at 25-35° and most preferably at 25-30° C. and dried at 60° C. for 5-20 hours to get Sunitinib base (I) as orange crystalline solid.

Accordingly, the present invention provides a complete physical characterization data (like Powdered X-Ray diffraction, FTIR, and DSC) for Sunitinib base obtained in polar aprotic solvents like ethyl acetate, methyl acetate or isopropyl acetate Accordingly, the present invention provides the crystalline Form-E obtained in polar aprotic solvents like ethyl acetate, methyl acetate or isopropyl acetate.

According to the process of the present invention, 5-Formyl-2,4-dimethyl-1H-pyrrole-3-carboxylic acid (2-diethylaminoethyl)-amide (IX) and 5-Fluoro-1,3-dihydro-indol-2-one (X) in dipolar aprotic solvents like tetrahydrofuran, 1,4-dioxane is reacted in presence of catalytic amount of pyrrolidine as base at reflux temperature for 6-15 hours. The resultant Sunitinib base is again triturated with the same solvent at reflux temperature for 1-2 hours and isolated at a temperature ranging from 20-45° C., preferably at 25-35° and most preferably at 25-30° C. and dried at 60° C. for 5-20 hours to get Sunitinib base (I) as orange crystalline solid.

Accordingly, the present invention provides a complete physical characterization data (like Powdered X-Ray diffraction, FTIR, and DSC) for Sunitinib base obtained in dipolar aprotic solvents tetrahydrofuran or 1,4-dioxane.

Accordingly, the present invention provides the crystalline Form-F obtained in dipolar aprotic solvent like tetrahydrofuran or 1,4-dioxane.

According to the process of the present invention, 5-Formyl-2,4-dimethyl-1H-pyrrole-3-carboxylic acid (2-diethylaminoethyl)-amide (IX) and 5-Fluoro-1,3-dihydro-indol-2-one (X) in ether solvents like diethyl ether, isopropyl ether or methyl tertiary butyl ether are reacted in presence of catalytic amount of pyrrolidine as base at reflux temperature for 3-9 hours. The resultant Sunitinib base is again triturated with the same solvent at reflux temperature for 1-2 hours and isolated at a temperature ranging from 20-45° C., preferably at 25-35° and most preferably at 25-30° C. and dried at 60° C. for 5-20 hours to get Sunitinib base (I) as orange crystalline solid.

Accordingly, the present invention provides a complete physical characterization data (like Powdered X-Ray diffraction, FTIR, and DSC) for Sunitinib base obtained in ether solvent like diethyl ether, diisopropyl ether or methyl tertiary butyl ether.

Accordingly, the present invention provides the crystalline Form-G obtained in ether solvent diethyl ether, diisopropyl ether or methyl tertiary butyl ether.

ADVANTAGES ASSOCIATED WITH THE PRESENT INVENTION i) The novel polymorphic forms (Form-A, Form-B, Form-C, Form-D, Form-E, Form-F, and Form-G) of Sunitinib base (I) of this invention may be used as alternate drug substances with potential therapeutic benefits.
ii) Present invention discloses a commercially viable process for the preparation of novel polymorphic forms of Sunitinib base.
iii) The novel polymorphic forms of Sunitinib base are suitable for pharmaceutical use.

Having thus described the present invention with reference to certain preferred embodiments, the invention will be further illustrated by the examples, which follow. These examples are provided for illustrative purposes only and are not intended to limit the scope of the invention in any way.

EXAMPLES

Powder X-Ray diffraction patterns were measured on a Siemens D5000 x-ray powder diffractometer having a copper-Kα radiation (1.5406 Å), Melting points were determined using a Mettler Toledo 823$^E$ differential scanning calorimeter with standard crimped pans and a beating rate of 10.0° C./min. Residual solvent analysis for the product was done on Agilent 6890N chromatograph. All chemicals used are available from Aldrich Chemical Co., Milwaukee, Wis., unless otherwise specified. The intermediate compounds (5-Formyl-2,4-dimethyl-1H-pyrrole-3-carboxylic acid (2-diethylaminoethyl)-amide and 5-Fluoro-1,3-dihydro-indol-2-one) were prepared according to the experimental procedure given in WO 01/60814.

In all experiments, residual solvents were found to be within the solvent limits as per ICH guidelines.

Example 1

Preparation of N-[2-(diethylamino)ethyl]-5-[(5-fluoro-1,2-dihydro-2-oxo-3H-indol-3-ylidene)methyl-2,4-dimethyl-1H-pyrrole-3-carboxamide Sunitinib Base of Form-A 5-Formyl-2,4-dimethyl-1H-pyrrole-3-carboxylic acid (2-diethylaminoethyl)-amide (10.0 g 0.037 moles) and 5-Fluoro-1,3-dihydro-indol-2-one (5.41 g; 0.0358 moles) in ethanol were reacted in presence of catalytic amount of pyrrolidine (0.16 mL) as base at reflux temperature for 2-8 hours. The resultant Sunitinib base was triturated in ethanol at reflux temperature for 1-2 hours and isolated at 25-30° C. and dried at 60° C. for 5-20 hours to get Sunitinib base (I) as orange crystalline solid.

Yield: 11.8 g HPLC Purity: 99.5% DSC: 247.2° C.

Example 2

Preparation of N-[2-(diethylamino)ethyl]-5-[(5-fluoro-1,2-dihydro-2-oxo-3H-indol-3-ylidene)methyl-2,4-dimethyl-1H-pyrrole-3-carboxamide Sunitinib Base of Form-A 5-Formyl-2,4-dimethyl-1H-pyrrole-3-carboxylic acid (2-diethylaminoethyl)-amide (10.0 g 0.037 moles) and 5-Fluoro-1,3-dihydro-indol-2-one (5.41 g; 0.0358 moles) in methanol were reacted in presence of catalytic amount of pyrrolidine (0.16 mL) as base at reflux temperature for 2-8 hours. The resultant Sunitinib base was triturated in methanol at reflux temperature for 1-2 hours and isolated at 25-30° C. and dried at 60° C. for 5-20 hours to get Sunitinib base (I) as orange crystalline solid.

Yield: 12.0 g HPLC Purity: 99.5%

Powdered XRD: FIG. 1 FTIR: FIG. 2 DSC: Peak Max.: 244.9° C. (FIG. 3)

Example 3

Preparation of N-[2-(diethylamino)ethyl]-5-[(5-fluoro-1,2-dihydro-2-oxo-3H-indol-3-ylidene)methyl-2,4-dimethyl-1H-pyrrole-3-carboxamide Sunitinib Base of Form-B 5-Formyl-2,4-dimethyl-1H-pyrrole-3-carboxylic acid (2-diethylaminoethyl)-amide (5.0 g 0.018 moles) and 5-Fluoro-1,3-dihydro-indol-2-one (2.705 g; 0.018 moles) in n-hexane were reacted in presence of catalytic amount of pyrrolidine (0.08 mL) as base at reflux temperature for 2-8 hours. The resultant Sunitinib base was triturated in n-hexane at reflux temperature for 1-2 hours and isolated at 25-30° C. and dried at 60° C. for 5-20 hours to get Sunitinib base (I) as orange crystalline solid.

Yield: 6.5 g HPLC Purity: 96.0%

Powdered XRD: FIG. 4 FTIR: FIG. 5 DSC: Principal peak Max. 235.9° C. (FIG. 6)

Example 4

Preparation of N-[2-(diethylamino)ethyl]-5-[(5-fluoro-1,2-dihydro-2-oxo-3H-indol-3-ylidene)methyl-2,4-dimethyl-1H-pyrrole-3-carboxamide Sunitinib Base of Form-C 5-Formyl-2,4-dimethyl-1H-pyrrole-3-carboxylic acid (2-diethylaminoethyl)-amide (5.0 g 0.018 moles) and 5-Fluoro-1,3-dihydro-indol-2-one (2.705 g; 0.018 moles) in cyclohexane were reacted in presence of catalytic amount of pyrrolidine (0.08 mL) as base at reflux temperature for 2-8 hours. The resultant Sunitinib base was triturated in cyclohexane at reflux temperature for 1-2 hours and isolated at 25-30° C. and dried at 60° C. for 5-20 hours to get Sunitinib base (I) as orange crystalline solid.

Yield: 6.8 g HPLC Purity: 97.7%

Powdered XRD: FIG. 7 FTIR: FIG. 8 DSC: Principal Peak Max: 223.4° C. (FIG. 9)

Example 5

Preparation of N-[2-(diethylamino)ethyl]-5-[(5-fluoro-1,2-dihydro-2-oxo-3H-indol-3-ylidene)methyl-2,4-dimethyl-1H-pyrrole-3-carboxamide Sunitinib Base of Form-D 5-Formyl-2,4-dimethyl-1H-pyrrole-3-carboxylic acid (2-diethylaminoethyl)-amide (5.0 g 0.018 moles) and 5-Fluoro-1,3-dihydro-indol-2-one (2.705 g; 0.018 moles) in toluene were reacted in presence of catalytic amount of pyrrolidine (0.08 mL) as base at 80-85° for 2-8 hours. The resultant Sunitinib base was triturated in toluene at 80-85° for 1-2 hours and isolated at 25-30° C. and dried at 60° C. for 5-20 hours to get Sunitinib base (I) as orange crystalline solid.

Yield: 6.3 g HPLC Purity: 98.7%

Powdered XRD: FIG. 10 FTIR: FIG. 11 DSC: Principal Peak Max.: 237.4° C. (FIG. 12)

Example 6

Preparation of N-[2-(diethylamino)ethyl]-5-[(5-fluoro-1,2-dihydro-2-oxo-3H-indol-3-ylidene)methyl-2,4-dimethyl-1H-pyrrole-3-carboxamide Sunitinib Base of Form-E 5-Formyl-2,4-dimethyl-1H-pyrrole-3-carboxylic acid (2-diethylaminoethyl)-amide (5.0 g 0.018 moles) and 5-Fluoro-1,3-dihydro-indol-2-one (2.705 g; 0.018 moles) in isopropyl acetate were reacted in presence of catalytic amount of pyrrolidine (0.08 mL) as base at reflux temperature for 2-8 hours. The resultant Sunitinib base was triturated in isopropyl acetate at reflux temperature for 1-2 hours and isolated at 25-30° C. and dried at 60° C. for 5-20 hours to get Sunitinib base (I) as orange crystalline solid.

Yield: 5.3 g HPLC Purity: 99.1%

Powdered XRD: FIG. 13 FTIR: FIG. 14 DSC: Principal peak Max. 226.9° C. (FIG. 15)

Example 7

Preparation of N-[2-(diethylamino)ethyl]-5-[(5-fluoro-1,2-dihydro-2-oxo-3H-indol-3-ylidene)methyl-2,4-dimethyl-1H-pyrrole-3-carboxamide Sunitinib Base of Form-F 5-Formyl-2,4-dimethyl-1H-pyrrole-3-carboxylic acid (2-diethylaminoethyl)-amide (5.0 g 0.018 moles) and 5-Fluoro-1,3-dihydro-indol-2-one (2.705 g; 0.018 moles) in tetrahydrofuran were reacted in presence of catalytic amount of pyrrolidine (0.08 mL) as base at reflux temperature for 2-8 hours. The resultant Sunitinib base was triturated in tetrahydrofuran at reflux temperature for 1-2 hours and isolated at 25-30° C. and dried at 60° C. for 5-20 hours to get Sunitinib base (I) as orange crystalline solid.

Yield: 2.0 g HPLC Purity: 99.5%

Powdered XRD: FIG. 16 FTIR: FIG. 17 DSC: Peak Max.: 242.5° C. (FIG. 18)

Example 8

Preparation of N-[2-(diethylamino)ethyl]-5-[(5-fluoro-1,2-dihydro-2-oxo-3H-indol-3-ylidene)methyl-2,4-dimethyl-1H-pyrrole-3-carboxamide Sunitinib Base of Form-G 5-Formyl-2,4-dimethyl-1H-pyrrole-3-carboxylic acid (2-diethylaminoethyl)-amide (5.0 g 0.018 moles) and 5-Fluoro-1,3-dihydro-indol-2-one (2.705 g; 0.018 moles) in methyl tertiary butyl ether were reacted in presence of catalytic amount of pyrrolidine (0.08 mL) as base at reflux temperature for 2-8 hours. The resultant Sunitinib base was triturated in methyl tertiary butyl ether at reflux temperature for 1-2 hours and isolated at 25-30° C. and dried at 60° C. for 5-20 hours to get Sunitinib base (I) as orange crystalline solid.

Yield: 6.4 g HPLC Purity: 99.527%

Powdered XRD: FIG. 19 FTIR: FIG. 20 DSC: Principal Peak Max.: 240.1° C. (FIG. 21)

We claim:

1. A crystalline form of Sunitinib base (I),

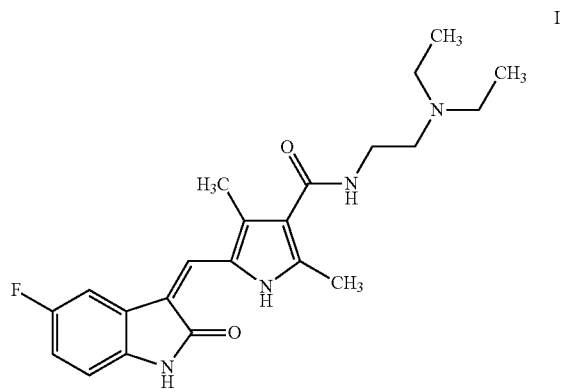 [SMILES: CCN(CC)CCNC(=O)c1c(C)[nH]c(/C=C2\C(=O)Nc3ccc(F)cc32)c1C]

which is Form C, wherein
Form C has
a powder X-Ray diffraction pattern having 2θ values of 4.3, 7.7, 8.6, 10.8, 12.9, 13.8, 17.3, 17.8, 19.1, 21.2, 21.5, 22.0, 23.2, 26.2, 27.6, 32.1, and 33.9; or
a FTIR spectrum having peaks at $cm^{-1}$ values of 3299.9, 1674.2, 1626.5, 1565.6, 1537.1, 1476.7, 1326.8, 1199.9, 1144.2, 797.1, 667.6, 606.9, and 589.0; or
a DSC curve having a principal peak maximum at 223.5° C.

2. A process for preparation of a crystalline form of Sunitinib base (I),

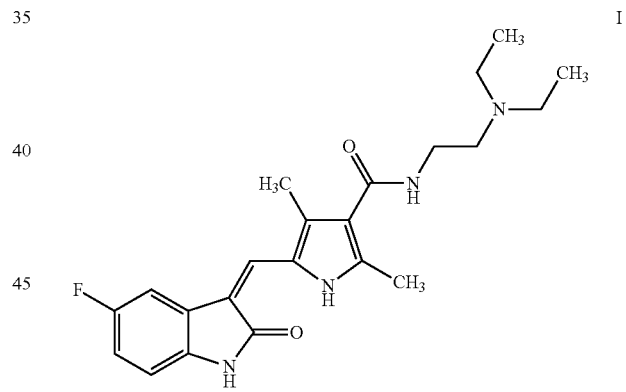

which comprises reaction of 5-Formyl-2,4-dimethyl-1H-pyrrole-3-carboxylic acid (2-diethylaminoethyl)-amide and 5-Fluoro-1,3-dihydro-indol-2-one in an organic solvent, wherein
the organic solvent is selected from non-polar organic solvents, preferably cyclopentane, cyclohexane or cycloheptane, and the crystalline form is Form C.

3. A process according to claim 2 wherein a catalyst is employed chosen from ammonia, alkali metal or alkaline earth hydroxides, carbonates, phosphates, bicarbonates, alkali metal hydroxides, methanolic or ethanolic ammonia, quaternary ammonium salts, silica gel, sodium acetate, ammonium acetate, Lewis acids, piperidine, piperazine, pyrrolidine, sodium ethoxide, sodium methoxide, and para toluene sulfonic acid (PTSA).

4. The process of claim 3 wherein the catalyst is selected from sodium hydroxide, potassium hydroxide, calcium hydroxide, magnesium hydroxide, barium hydroxide, tetrabutyl ammonium hydroxide, benzyl trimethyl ammonium hydroxide and boron trifluerride etherate.

5. A method of preparing a pharmaceutically acceptable salt of Sunitinib, which method comprises salifying a crystalline form as defined in claim 1.

6. A method of treating cancer in a subject, which method comprises administering to the said subject an effective amount of a crystalline form as defined in claim 1, and wherein said cancer is selected from gastrointestinal stromal tumors and advanced renal cell carcinoma.

* * * * *